US011959124B2

(12) United States Patent
Grant et al.

(10) Patent No.: US 11,959,124 B2
(45) Date of Patent: *Apr. 16, 2024

(54) METHODS AND SYSTEMS FOR DETERMINING ADAMTS13 ENZYME ACTIVITY

(71) Applicant: Laboratory Corporation of America Holdings, Burlington, NC (US)

(72) Inventors: Russell Philip Grant, Chapel Hill, NC (US); Christopher Michael Shuford, Mebane, NC (US); Meghan Norris Bradley, Mebane, NC (US)

(73) Assignee: Laboratory Corporation of America Holdings, Burlington, NC (US)

(*) Notice: Subject to any disclaimer, the term of this patent is extended or adjusted under 35 U.S.C. 154(b) by 495 days.

This patent is subject to a terminal disclaimer.

(21) Appl. No.: 17/088,778

(22) Filed: Nov. 4, 2020

(65) Prior Publication Data

US 2021/0062242 A1 Mar. 4, 2021

Related U.S. Application Data

(63) Continuation of application No. 15/730,165, filed on Oct. 11, 2017, now Pat. No. 10,858,689.

(60) Provisional application No. 62/406,693, filed on Oct. 11, 2016.

(51) Int. Cl.
   *C12Q 1/37* (2006.01)
   *C12Q 1/00* (2006.01)
   *G01N 33/68* (2006.01)

(52) U.S. Cl.
   CPC .............. *C12Q 1/37* (2013.01); *C12Q 1/005* (2013.01); *G01N 33/6851* (2013.01); *G01N 2333/96486* (2013.01); *G01N 2560/00* (2013.01); *G01N 2800/226* (2013.01)

(58) Field of Classification Search
   None
   See application file for complete search history.

(56) References Cited

U.S. PATENT DOCUMENTS

| 7,718,763 | B2 | 5/2010 | Miyata et al. |
| 7,833,726 | B2 | 11/2010 | Kato et al. |
| 8,623,612 | B2 | 1/2014 | Varadi et al. |
| 8,637,268 | B2 | 1/2014 | Chen et al. |
| 8,759,018 | B2 | 6/2014 | Ono et al. |
| 8,932,820 | B2 | 1/2015 | Althaus et al. |
| 9,110,085 | B2 | 8/2015 | Varadi et al. |
| 9,297,815 | B2 | 3/2016 | Igami et al. |
| 10,202,633 | B2 | 2/2019 | Gian et al. |
| 10,209,263 | B2 | 2/2019 | Varadi et al. |
| 10,858,689 | B2 | 12/2020 | Grant et al. |
| 2008/0206787 | A1 | 8/2008 | Wu et al. |
| 2012/0142036 | A1 | 6/2012 | Chen et al. |
| 2019/0145989 | A1 | 5/2019 | Varadi et al. |

FOREIGN PATENT DOCUMENTS

| AU | 2009322367 B2 | 3/2015 |
| CA | 2745805 A1 | 6/2010 |
| CA | 2855498 A1 | 5/2013 |
| CN | 101613688 A | 12/2009 |
| CN | 102533937 A | 7/2012 |
| CN | 106771230 A | 5/2017 |
| CN | 108463729 A | 8/2018 |
| EP | 1779117 B1 | 5/2010 |
| EP | 1990421 B1 | 6/2012 |
| EP | 2776461 B1 | 2/2018 |
| EP | 3401685 A1 | 11/2018 |
| JP | 5221333 B2 | 6/2006 |
| JP | 3944586 B2 | 7/2007 |
| JP | 4820192 B2 | 11/2011 |
| JP | 2012082210 | 4/2012 |
| JP | 2017153490 A | 9/2017 |
| JP | 6419576 B2 | 11/2018 |
| JP | WO2017/119498 A1 | 12/2018 |
| KR | 101366724 B1 | 2/2014 |
| WO | 2006085441 | 8/2006 |
| WO | 2018/071502 | 4/2018 |
| WO | 2018/100053 A1 | 6/2018 |
| WO | 2018/203086 A1 | 11/2018 |

OTHER PUBLICATIONS

AU2017343623, "First Examination Report", dated Jan. 31, 2023, 5 pages.
AU2017343623, "Second Examination Report", dated Mar. 15, 2023, 4 pages.
CN 201780062891.5, Office Action, dated Oct. 31, 2022, 8 pages.
U.S. Appl. No. 15/730,165, Final Office Action, dated Apr. 9, 2020, 25 pages.
U.S. Appl. No. 15/730,165, Non-Final Office Action, dated Oct. 1, 2019, 17 pages.
U.S. Appl. No. 15/730,165, Notice of Allowance, dated Jul. 29, 2020, 9 pages.
CA 3,038,122, Office Action, dated Feb. 6, 2020, 4 pages.
EP 17791243.3, Office Action, dated Jun. 15, 2020, 4 pages.
PCT/US2017/056080, International Preliminary Report on Patentability, dated Apr. 25, 2019, 9 pages.
Adcock et al., "Effect of 3.2% vs 3.8% Sodium Citrate Concentration on Routine Coagulation Testing", American Journal of Clinical Pathology, 107(1):105-110 (1997).
Adcock et al., Collection, Transport, and Processing Blood Specimens for Testing Plasma-Based Coagulation Assays and Molecular Hemostasis Assays; Approved Guideline—Fifth Edition, 28(5):1-48 (2008).

(Continued)

*Primary Examiner* — Suzanne M Noakes
*Assistant Examiner* — Jae W Lee
(74) *Attorney, Agent, or Firm* — Kilpatrick Townsend & Stockton LLP

(57) ABSTRACT

Disclosed are methods and systems for the analysis activity of enzyme disintegrin and metalloproteinase with a thrombospondin type 1 motif, member 13 (ADAMTS13) in a sample. The methods and systems disclosed herein can be useful for diagnosis of thrombotic thrombocytopenic purpura in a patient.

29 Claims, 4 Drawing Sheets

Specification includes a Sequence Listing.

(56) References Cited

OTHER PUBLICATIONS

Angel, T. et al., "Mass spectrometry based proteomics: existing capabilities and future directions," Chem Soc Rev. 41(10):3912-3928 (2012).
Clarke, W. et al., "Challenges in implementing clinical liquid chromatography-tandem mass spectrometry methods—seeking the light at the end of the tunnel," J. Mass Spectrom. 48:755-767 (2013).
Connell, N. et al., "Effect of ADAMTS13 activity turnaround time on plasma utilization for suspected thrombotic thrombocytopenia purpura," Transfusion 56:354-359 (2016).
Froehlich-Zahnd et al., "Evidence for a role of anti-ADAMTS13 autoantibodies despite normal ADAMTS13 activity in recurrent thrombotic thrombocytopeniarpura", Haematologica, 97(2):297-303 (2012).
Gottfried et al., "Prothrombin Time and Activated Partial Thromboplastin Time Can be Performed on the First Tube", American Journal of Clinical Pathology, 107(6):681-683 (1997).
Hovinga et al., "Survival and relapse in patients with thrombotic thrombocytopenia purpura", Blood, 115(8):1500-1500 (2010).
Jannetto, P. and Fitzgerald, R., "Effective Use of Mass Spectrometry in the Clinical Laboratory," Clinical Chem. 62(1):92-98 (2016).
Jin et al., "A Rapid Test for the Diagnosis of Thrombotic Thrombocytopeniarpura using Surface Enhanced Laser Desorption-Ionization Time-of-Flight (SELDI-TOF)-Mass Spectrometry", Journal of Thrombosis and Haemostasis, 4(2):333-338 (2006).
Kokame et al., "VWF73, A region from D1596 to R1668 of Von Willebrand Factor provides a Minimal Substrate for ADAMTS-13", Blood, 56th Annual Meeting of the American-Society-of-Hematology, 103(2):607-612 (2004).
Kato et al., "Novel monoclonal antibody-based enzyme immunoassay for determining plasma levels of ADAMTS13 activity", Transfusion, 46:1444-1452 (2006).
Lammie et al., "Acquired thrombotic thrombocytopenic purpura: ADAMTS13 activity, anti-ADAMTS13 autoantibodies and risk of recurrent disease", Haematologica, 93(2):172-177 (2008).
Loirat, et al., "Atypical hemolytic uremic syndrome", Orphanet Journal of Rare Diseases, 6(1):1-30 (2011).
Lotta, L. et al., "Residual plasmatic activity of ADAMTS13 is correlated with phenotype severity in congenital thrombotic thrombocytopenic purpura," Blood 120(2):440-448 (2012).
Mannucci et al., "TTP and ADAMTS13: When Is Testing Appropriate?", Hematology, pp. 121-126 (2007).
Mcglasson et al., "Drawing Specimens for Coagulation Testing: Is a Second Tube Necessary?", Clinical Laboratory Science Journal of the American Society for Medical Technology, 12(3):137-139 (1999).
Moake, Thrombotic thrombocytopenia purpura (TTP) and other thrombotic microangiopathies, Best Practice & Research Clinical Haematology, 22(4):567-576 (2009).
Peyvandi et al., "ADAMTS13 and anti-ADAMTS13 antibodies as markers for recurrence of acquired thrombotic thrombocytopenic purpura during remission," Haematologica, 93(2):232-239 (2008).
Rieger et al., "ADAMTS13 autoantibodies in patients with thrombotic microangiopathies and other immunomediated diseases", Blood, 106(4):1262-1267 (2005).
Reneke et al., "Prolonged Prothrombin Time and Activated Partial Thromboplastin Time Due to Underfilled Specimen Tubes with 109 mmol/L (3.2%) Citrate Anticoagulant", American Journal of Clinical Pathology, 109(6):754-757 (1998).
Sadler, "Von Willebrand factor, ADAMTS13, and thrombotic thrombocytopenic purpura", Blood, 112(1):11-19 (2008).
Scheiflinger et al., "Nonneutralizing IgM and IgG antibodies to von Willebrand factor-cleaving protease (ADAMTS-13) in a patient with thrombotic thrombocytopenic purpura", Blood, 102(9):3241-3243 (2003).
Scully, "Inhibitory anti-ADAMTS13 antibodies: measurement and clinical application", Blood Reviews, 24(1):11-16 (2010).
Shelat et al., "Inhibitory autoantibodies against ADAMTS-13 in patients with thrombotic thrombocytopenic purpura bind ADAMTS-13 protease and may accelerate it clearance in vivo", Journal of Thrombosis and Haemostasis, 4(8):1707-1717 (2006).
Tsai, "Pathophysiology of thrombotic thrombocytopenic purpura", International Journal Hematology, 91(1):1-19 (2010).
Van Den Broek, I. and Fitzgerald, R., "LC-MS-based quantification of intact proteins: perspective for clinical and bioanalytical applications," Bioanalysis 7(15):1943-1958 (2015).
Wang et al., "Hypochlorous Acid Generated by Neutrophils Inactivates Adamts13: An Oxidative Mechanism for Regulating Adamts13 Proteolytic Activity during Inflammation", Journal of Biological Chemistry, 290(3):1422-1431 (2015).
Waters et al., "aHUS caused by complement dysregulation: new therapies on the horizon", Pediatric Nephrology, 26(1):41-57 (2011).
Waugh, D., "An overview of enzymatic reagents for the removal of affinity tages," Protein Expression and Purification 80:283-293 (2011).
Zheng et al., "Effect of plasma exchange on plasma ADAMTS13 metalloprotease activity, inhibitor level, and clinical outcome in patients with idiopathic and nonidiopathic thrombotic thrombocytopenic purpura", 103(11):4043-4049 (2004).
Zheng et al., "Pathogenesis of Thrombotic Microangiopathies", Annual Review of Pathology Mechanisms of Disease, 3:249-277 (2008).
PCT/US2017/056080, "International Search Report and Written Opinion", dated Dec. 19, 2017.
Bredehoft, M. et al., "Quantification of Human Insulin-like Growth Factor-1 and Qualitative Detection of Its Analogues in Plasma Using Liquid Chromatography/Electrospray Ionisation Tandem Mass Spectrometry", Rapid Commun. Mass Spectrom., 22(4):477-485 (2008).
CA 3,038,122, Office Action, dated Feb. 12, 2021, 4 pages.
EP 17791243.3, Office Action, Aug. 25, 2021, 5 pages.
KR 10-2019-7013181, Office Action, dated Aug. 27, 2021, 6 pages.
JP 2019-519274, Office Action, dated Feb. 25, 2022, 10 pages.
CA 3,038,122, Office Action, dated Dec. 23, 2021, 3 pages.
CA 3,038,122, Office Action, dated Jan. 9, 2023, 5 pages.
EP 17791243.3, Office Action, dated Dec. 22, 2022, 5 pages.
JP 2019-519274, Office Action, dated Jun. 18, 2021, 13 pages.
U.S. Appl. No. 15/730,165, Advisory Action, dated Jun. 19, 2020, 17 pages.
CN201780062891.5 , "Office Action", dated May 15, 2023, 11 pages.
Japanese Application No. 2019-519274, Office Action mailed on Oct. 11, 2023, 32 pages (8 pages of Original Document and 24 pages of English Translation).
Kadota et al., Importance of Ionization Method in Mass Spectrometry, Journal of the Society for Biotechnology, vol. 91, No. 3, 2013, pp. 133-136.
Kokame, Measurement of ADAMTS13, Japanese Journal of Thrombosis and Hemostasis, vol. 18, No. 3, 2007, pp. 234-240.
Yasuda, Analysis of Protein/Peptide Hormone by Capillary LC-MS, Newsletter of Japan Society for Comparative Endocrinology, No. 107, 2002, pp. 29-35.

FIG. 1

VWF A2 Domain
1459-1668
(SEQ ID NO: 2)

ADAMTS13
cleavage site
1605-1606

ADAMTS13
exosite
1660-1668

```
>sp|P04275|764-2813 Mature VWF - SEQ ID NO: 1
 764 SLSCRPPMVKLVCPADNLRAEGLECTKTCQNYDLECMSMGCVSGCLCPPGMVRHENRCVA    823
 824 LERCPCFHQGKEYAPGETVKIGCNTCVCQDRKWNCTDHVCDATCSTIGMAHYLTFDGLKY    883
 884 LFPGECQYVLVQDYCGSNPGTFRILVGNKGCSHPSVKCKKRVTILVEGGEIELFDGEVNV    943
 944 KRPMKDETHFEVVESGRYIILLLGKALSVVWDRHLSISVVLKQTYQEKVCGLCGNFDGIQ   1003
1004 NNDLTSSNLQVEEDPVDFGNSWKVSSQCADTRKVPLDSSPATCHNNIMKQTMVDSSCRIL   1063
1064 TSDVFQDCNKLVDPEPYLDVCIYDTCSCESIGDCACFCDTIAAYAHVCAQHGKVVTWRTA   1123
1124 TLCPQSCEERNLRENGYECEWRYNSCAPACQVTCQHPEPLACPVQCVEGCHAHCPPGKIL   1183
1184 DELLQTCVDPEDCPVCEVAGRRFASGKKVTLNPSDPEHCQICHCDVVNLTCEACQEPGGL   1243
1244 VVPPTDAPVSPTTLYVEDISEPPLHDFYCSRLLDLVFLLDGSSRLSEAEFEVLKAFVVDM   1303
1304 MERLRISQKWVRVAVVEYHDGSHAYIGLKDRKRPSELRRIASQVKYAGSQVASTSEVLKY   1363
1364 TLFQIFSKIDRPEASRITLLLMASQEPQRMSRNFVRYVQGLKKKKVIVIPVGIGPHANLK   1423
1424 QIRLIEKQAPENKAFVLSSVDELEQQRDEIVSYLCDLAPEAPPPTLPPDMAQVTVGPGLL   1483
1484 GVSTLGPKRNSMVLDVAFVLEGSDKIGEADFNRSKEFMEEVIQRMDVGQDSIHVTVLQYS   1543
1544 YMVTVEYPFSEAQSKGDILQRVREIRYQGGNRTNTGLALRYLSDHSFLVSQGDREQAPNL   1603
1604 VYMVTGNPASDEIKRLPGDIQVVPIGVGPNANVQELERIGWPNAPILIQDFETLPREAPD   1663
1664 LVLQRCCSGEGLQIPTLSPAPDCSQPLDVILLLDGSSSFPASYFDEMKSFAKAFISKANI   1723
1724 GPRLTQVSVLQYGSITTIDVPWNVVPEKAHLLSLVDVMQREGGPSQIGDALGFAVRYLTS   1783
1784 EMHGARPGASKAVVILVTDVSVDSVDAAADAARSNRVTVFPIGIGDRYDAAQLRILAGPA   1843
1844 GDSNVVKLQRIEDLPTMVTLGNSFLHKLCSGFVRICMDEDGNEKRPGDVWTLPDQCHTVT   1903
1904 CQPDGQTLLKSHRVNCDRGLRPSCPNSQSPVKVEETCGCRWTCPCVCTGSSTRHIVTFDG   1963
1964 QNFKLTGSCSYVLFQNKEQDLEVILHNGACSPGARQGCMKSIEVKHSALSVELHSDMEVT   2023
2024 VNGRLVSVPYVGGNMEVNVYGAIMHEVRFNHLGHIFTFTPQNNEFQLQLSPKTFASKTYG   2083
2084 LCGICDENGANDFMLRDGTVTTDWKTLVQEWTVQRPGQTCQPILEEQCLVPDSSHCQVLL   2143
2144 LPLFAECHKVLAPATFYAICQQDSCHQEQVCEVIASYAHLCRTNGVCVDWRTPDFCAMSC   2203
2204 PPSLVYNHCEHGCPRHCDGNVSSCGDHPSEGCFCPPDKVMLEGSCVPEEACTQCIGEDGV   2263
2264 QHQFLEAWVPDHQPCQICTCLSGRKVNCTTQPCPTAKAPTCGLCEVARLRQNADQCCPEY   2323
2324 ECVCDPVSCDLPPVPHCERGLQPTLTNPGECRPNFTCACRKEECKRVSPPSCPPHRLPTL   2383
2384 RKTQCCDEYECACNCVNSTVSCPLGYLASTATNDCGCTTTTCLPDKVCVHRSTIYPVGQF   2443
2444 WEEGCDVCTCTDMEDAVMGLRVAQCSQKPCEDSCRSGFTYVLHEGECCGRCLPSACEVVT   2503
2504 GSPRGDSQSSWKSVGSQWASPENPCLINECVRVKEEVFIQQRNVSCPQLEVPVCPSGFQL   2563
2564 SCKTSACCPSCRCERMEACMLNGTVIGPGKTVMIDVCTTCRCMVQGVISGFKLECRKTT   2623
2624 CNPCPLGYKEENNTGECCGRCLPTACTIQLRGGQIMTLKRDETLQDGCDTHFCKVNERGE   2683
2684 YFWEKRVTGCPPFDEHKCLAEGGKIMKIPGTCCDTCEEPECNDITARLQYVKVGSCKSEV   2743
2744 EVDIHYCQGKCASKAMYSIDINDVQDQCSCCSPTRTEPMQVALHCTNGSVVYHEVLNAME   2803
2804 CKCSPRKCSK
```

FIG. 2 vWF A2 Domain

VWF A2 Domain
SEQ ID NO: 2

ADAMTS13 cleavage site

ADAMTS13 exosite

```
1484 GVSTLGPKRNSMVLDVAFVLEGSDKIGEADFNRSKEFMEEVIQRMDVGQDSIHVTVLQYS        1543
1544 YMVTVEYPFSEAQSKGDILQRVREIRYQGGNRTNTGLALRYLSDHSFLVSQDREQAPNL        1603
1604 TGNPASDEIKRLPGDIQVVPIGVGPNANVQELERIGWPNAPILIQDFETLPREAPD          1663
1664 LAPEAPPPTLPPDMAQVTVGPGLL                                          1483
      YMV
      KVLQR
``` vWF73 Substrate
(8085.1 Da)
SEQ ID NO: 3

```
                                          DREQAPNL 1603    ADAMTS13
                                                           cleavage site
1604 VYMVTGNPASDEIKRLPGDIQVVPIGVGPNANVQELERIGWPNAPILIQDFETLPREAPD 1663   ADAMTS13
1664 LVLQR  (SEQ ID NO: 3)                                  exosite
```

DREQAPNLVY
(SEQ ID NO: 4)

METHODS AND SYSTEMS FOR DETERMINING ADAMTS13 ENZYME ACTIVITY

CROSS REFERENCE TO RELATED APPLICATION

This application is a continuation of U.S. patent application Ser. No. 15/730,165, filed Oct. 11, 2017, which claims the benefit of U.S. Provisional Application No. 62/406,693, filed Oct. 11, 2016. The contents of the above applications are incorporated by reference in their entirety herein.

FIELD OF THE INVENTION

The present invention relates to methods and systems for determining the activity of ADAMTS13 (a disintegrin and metalloproteinase with a thrombospondin type 1 motif, member 13), which can be useful for diagnosis of thrombotic thrombocytopenic purpura in a patient.

BACKGROUND

Thrombotic thrombocytopenic purpura (TTP) is a blood disorder that causes blood clots to form in small blood vessels. This leads to a low platelet count (thrombocytopenia), while the clots can damage many organs, including the kidneys, heart and brain. Without treatment, the fatality rate for TTP is about 90%. The typical treatment is plasma exchange, which reduces the fatality rate to about 10% at six months.

Most cases of TTP arise from reduced activity of ADAMTS13, which is a protease that specifically cleaves blood glycoprotein von Willebrand factor (vWF). ADAMTS13 specifically cleaves vWF between tyrosine-1605 and methionine-1606 under circulatory conditions of high shear stress. ADAMTS13 has also been referred to as von Willebrand factor-cleaving protease. Both congenital and acquired (autoimmune) deficiency of ADAMTS13 activity are characterized by the presence of unusually large vWF factor multimers that are more platelet adhesive than smaller multimers found in normal plasma, resulting in TTP.

Most TTP cases are idiopathic and are associated with antibodies to ADAMTS13 that reduce circulating functional enzyme levels through increased clearance of ADAMTS13 from circulation or direct inhibition of ADAMTS13 proteolytic activity, although antibodies to ADAMTS13 are not usually detected in patients with congenital deficiency. Studies have shown that quantitative immunoassays for IgG-specific autoantibodies to ADAMTS13 are more sensitive than the functional (i.e., inhibition) assays for detecting antibodies against ADAMTS13.

Symptomatically, TTP is characterized by thrombotic microangiopathy (TMA), the formation of blood clots in small blood vessels throughout the body, which can lead to microangiopathic hemolytic anemia and thrombocytopenia. Measurement of ADAMTS13 activity can play a role in differentiating TTP from a number of clinically similar conditions that have different underlying causes. These syndromes, which can be associated with pregnancy, organ transplantation and certain medications, generally do not exhibit significantly reduced ADAMTS13 activity levels. Hemolytic Uremic Syndrome (HUS) is clinically similar to TTP, but is associated with acute renal failure. Diarrhea-associated HUS accounts for most of cases and is usually caused by infection with Shiga-toxin-producing *Escherichia coli* (0157:H7). Diarrhea-negative or atypical HUS (aHUS) is thought to be caused by uncontrolled complement activation occurring in both children and adults and shares many of the clinical features of TTP; however, aHUS is not associated with severe reduction (i.e., <10%) of ADAMTS13 activity.

Indeed, congenital ADAMTS13 activity deficiency, also referred to as Upshaw-Schulman syndrome, is an autosomal recessive disorder that is associated with ADAMTS13 activity levels below 10% of normal ADAMTS13 activity. Disease classification based on clinical features alone can be unreliable and can result in inappropriate treatment or delay in the initiation of effective treatment. Therefore, in patients exhibiting laboratory evidence of thrombocytopenia and microangiopathic hemolysis, the measurement of ADAMTS13 activity can be invaluable in differentiating TTP from other clinically similar conditions.

Generally, lifesaving Total Plasma Exchange (TPE) therapy is initiated before ADAMTS13 activity testing when TTP is suspected based on clinical presentation because of the acuity and severity of the of the symptoms. In many cases TPE will be stopped if a normal ADAMTS13 activity test result is obtained. As such, the sooner ADAMTS13 test results are obtained, the sooner TPE therapy can be stopped, which 1) reduces the cost associated with (needless) TPE therapy and 2) allows the clinician to focus on alternative causes for the symptoms and thus appropriate therapies. (Connell, N. T. et al. *Transfusion* 2016, 56 (2), 354-359).

Thus, there is a need for improved lab tests to measure ADAMTS13 activity in samples from individuals at risk for or suspected of having TTP. There is a need for improved lab tests that are more cost-efficient, thereby allowing more frequent testing and also provide clinicians testing results sooner.

SUMMARY

The present invention provides methods and systems for determining activity of ADAMTS13, which can be useful for diagnosis of TTP in a patient. In certain embodiments, the invention comprises a method to measure ADAMTS13 by mass spectrometry and/or liquid chromatography-tandem mass spectroscopy (LC-MS/MS).

For example, in some embodiments, the invention comprises a method for determining ADAMTS13 enzyme activity in a sample, comprising: (a) incubating the sample with an exogenous peptide substrate for ADAMTS13 under conditions allowing for enzymatic cleavage of the exogenous peptide substrate by ADAMTS13 to produce an enzymatic cleavage product; (b) ionizing the enzymatic cleavage product to generate a multiply charged gas-phase ion of the cleavage product; and (c) analyzing said multiply charged gas-phase ion by mass spectrometry to determine the presence or amount of enzymatic cleavage product in the sample, wherein the presence or the amount of the product of the enzymatic cleavage product in the sample is indicative of the presence or the amount of the activity of ADAMTS13 in the sample.

In certain embodiments, the invention may comprise a method for determining an amount of activity of ADAMTS13 in a sample, comprising: (a) incubating the sample with a synthetic peptide substrate for ADAMTS13 and an isotopically labelled equivalent of a product peptide to the sample under conditions allowing for enzymatic cleavage of the synthetic peptide substrate by ADAMTS13; (b) terminating the enzymatic cleavage in the sample being incubated; (c) partially purifying an enzymatic cleavage product and the internal standard from other components of the sample using liquid chromatography or another purification technique; and (d) analyzing the partially purified enzymatic cleavage product and the standard by mass spectrometry to determine the amount of enzymatic cleavage product and the internal standard in the sample, wherein a ratio of the determined amounts of the enzymatic cleavage product and the internal standard is indicative of the amount of activity of ADAMTS13 in the sample.

In other embodiments, the invention may comprise a system for determining activity of ADAMTS13 in a sample, the system comprising: (a) a station for incubating the sample with an exogenous peptide substrate for ADAMTS13 under conditions allowing for enzymatic cleavage of the exogenous peptide substrate by ADAMTS13 to generate an enzymatic cleavage product; (b) a station for ionizing the enzymatic cleavage product to generate a multiply charged gas-phase ion of said cleavage product; and (c) a station for analyzing the multiply charged gas phase ion by mass spectrometry to determine the presence and/or amount of the enzymatic cleavage product in the sample, wherein the amount of the enzymatic cleavage product is indicative of the activity of ADAMTS13 in the sample. In some embodiments, the system may further comprise a station for partially purifying the enzymatic cleavage product. In an embodiment, the system may comprise a station for chromatographically separating the enzymatic cleavage product using liquid chromatography.

Both the methods and the systems of the invention may include various embodiments. For example, in certain embodiments, the method may comprise, after the incubation step but prior to the ionizing step, a step of partially purifying the enzymatic cleavage product, such that the ionizing step is performed on the partially purified enzymatic cleavage product. In certain embodiments, the system may comprise a station for performing such a step.

In an embodiment, the step of partially purifying the enzymatic cleavage product comprises centrifugation, and the ionizing step is performed on a supernatant comprising the enzymatic cleavage product. Additionally and/or alternatively, the step of partially purifying the enzymatic cleavage product may comprise liquid chromatography to generate an eluent comprising the enzymatic cleavage product and the ionizing step is performed on the eluent. Additionally and/or alternatively, the step of partially purifying the enzymatic cleavage product comprises capillary electrophoresis to generate an eluent comprising the enzymatic cleavage product and the ionizing step is performed on the eluent. Additionally and/or alternatively, the step of partially purifying the enzymatic cleavage product comprises solid phase extraction to generate an eluent comprising the enzymatic cleavage product and the ionizing step is performed on the eluent. Additionally and/or alternatively, the step of partially purifying the enzymatic cleavage product comprises filtration to generate an eluent comprising the enzymatic cleavage product and the ionizing step is performed on the eluent. Additionally and/or alternatively, the step of partially purifying the enzymatic cleavage product comprises filtration to generate a retained fraction comprising the enzymatic cleavage product and the ionizing step is performed on the retained fraction. Additionally and/or alternatively, the step of partially purifying the enzymatic cleavage product comprises the use of affinity enrichment of the enzymatic cleavage product and the ionizing step is performed on the affinity enriched enzymatic cleavage product. In certain embodiments, the affinity enrichment technique uses an immobilized metal affinity resin. For example, in various embodiments, the affinity enrichment technique may utilize an antibody or a fragment of an antibody, such as a Fab fragment. Or, the affinity enrichment technique may utilize streptavidin. Or, the affinity enrichment technique may utilize protein-G, or protein-A. Or, the affinity enrichment technique may utilize an aptamer.

In certain embodiments, the methods and systems include a step for terminating the incubation prior to analysis and/or partial purification. For example, in certain embodiments, the methods and/or systems may include a step (or a station for performing such a step) of terminating the enzymatic cleavage in the sample being incubated. In certain embodiments, the terminating step may comprise adding a precipitating reagent to the sample being incubated. A variety of precipitating reagents may be used. Thus, in alternate embodiments, the precipitating reagent may comprise methanol, and/or acetonitrile, and/or acetone, and/or 2-propanol, and/or sulfate, and/or trichloroacetic acid, and/or perchloric acid. In certain embodiments, termination of the reaction is performed by changing the pH to a range outside of the range suitable for the enzyme to be functional. For example, the terminating step may comprise adjusting the pH of the sample being incubated below pH 5, or alternatively to above pH 9. In certain embodiments, the terminating step may comprise adjusting the temperature to a range outside of the range suitable for the enzyme to be functional. For example, the terminating step may comprise heating the sample being incubated to a temperature above 50 degrees centigrade or alternatively, cooling the sample being incubated to a temperature below 15 degrees centigrade. In certain embodiments, the terminating step may comprise adding an inhibitor of ADAMTS13 to the sample being incubated. For example, in one embodiment, the inhibitor may be ethylenediaminetetraacetic acid (EDTA).

The substrate used in the reaction is designed to allow for measurement of the activity of ADAMTS13. In certain embodiments, the substrate includes the von Willebrand Factor A2 Domain (vWF A2 Domain), or a portion thereof. In an embodiment, the exogenous peptide substrate has at least 70% sequence identity to vWF amino acid sequence or a portion thereof. In certain embodiments, the substrate comprises a functional ADAMTS13 cleavage site. In an embodiment, the substrate comprises a functional ADAMTS13 exosite. In an embodiment, the substrate comprises an exogenous peptide. The exogenous peptide may be a synthetic peptide. For example, in an embodiment, the exogenous substrate is a synthetic peptide having at least 70% sequence similarity to amino acid sequence of vWF73 (SEQ ID NO: 3). In an embodiment, the peptide is SEQ ID NO: 3.

In some embodiments, the peptide substrate comprises one or more affinity tags. In some embodiments, the one or more affinity tags are selected from the group consisting of: MYC-tag, FLAG-tag, polyHis-tag, or GST-tag. In some embodiments, the one or more affinity tags contain the epitope for an antibody. Additionally and/or alternatively, the exogenous peptide substrate may comprise one or more non-natural amino acids. In certain embodiments, the one or more non-natural amino acids are biotinylated. In certain embodiments, the one or more non-natural amino acids are stable isotopically labeled amino acids.

The substrate is, upon incubation with ADAMTS13, cleaved into two smaller peptides. The resulting products depends on the peptide used as an exogenous substrate. For example, using the exogenous substrate of SEQ ID NO: 3 (or a substrate having additional or fewer amino acids at the N-terminal end) the enzymatic cleavage product may comprise a peptide having a sequence of DREQAPNLVY (SEQ ID NO: 4). It is contemplated that other products may be formed where there are additional amino acids on the C-terminal end of the substrate peptide.

The ionization step results in the formation of multiply charged ions. In certain embodiments, the ionization step includes ionizing the enzymatic cleavage product using an ionization technique, such as electrospray ionization, atmospheric pressure chemical ionization or atmospheric pressure photoionization. An ionization technique can be selected from the group consisting of: electrospray ionization, atmospheric pressure chemical ionization and atmospheric pressure photoionization.

The analyzing step allows for characterization and quantification of the multiply charged ions formed in the ionization step. In certain embodiments, the analyzing step includes determining the specific activity of the ADAMTS13. In some embodiments, the analyzing step uses tandem mass spectrometry. Using the substrate of SEQ ID NO: 3 to generate the product of SEQ ID NO: 4, the analyzing step may, in certain embodiments, use ions having an m/z selected from the group consisting of 602.8±2, 182.1±2, 281.1±2, 462.7±2, 512.3±2, 600.3±2, 605.3±2, 811.4±2, 924.5±2 and 1023.5±2.

As noted above, the methods and systems of the invention may employ an internal standard. In some embodiments, the internal standard is added prior to the ionization step. Alternatively, the internal standard may be added concurrently with the substrate. In yet other embodiments, the internal standard may be added to the sample prior to the incubation step. Or, the internal standard may be added to the sample being incubated. In certain embodiments, the presence or amount of the internal standard is determined along with the presence or amount of the enzymatic cleavage product. In certain embodiments, the ratio between the determined amount of the internal standard and the determined amount of the enzymatic cleavage product is indicative of the amount of the enzymatic cleavage product formed. In some embodiments, the ratio between the determined amount of the internal standard and the determined amount of the enzymatic cleavage product is indicative of the amount of activity (e.g., the specific activity) of ADAMTS13 in the sample.

A variety of internal standards may be used. In some embodiments, the internal standard is a different peptide than the cleavage product. In some other embodiments, however, the internal standard is an isotopically labelled equivalent of the enzymatic cleavage product.

A variety of biological samples may be used. In certain embodiments, the sample is a biological fluid obtained from a patient. For example, the biological fluid may be plasma or serum. Or other types of biological fluids (e.g., saliva, sputum, sweat, cerebral spinal fluid) may be used.

In some embodiments, the methods and systems may employ, either before or after the optional partial purification step, but after the termination step, a step (and/or a station for performing such a step) of modifying the molecular structure of the enzymatic cleavage in the sample being incubated. For example, in certain embodiments, the modifying step may comprises further hydrolyzing the enzymatic cleavage product. For example, the hydrolysis may be performed using an enzyme. In certain embodiments, the enzyme may be one of trypsin, pepsin, or LysC. Or, other enzymes may be used. In other embodiments, the hydrolysis may be performed using a chemical reagent. For example, the chemical reagent may be one of formic acid or cyanogen bromide. Or, other chemical reagents may be used. In some embodiments, the enzymatic cleavage product may be derivatized. For example, in some embodiments, the derivatization is enzymatically catalyzed. Or, the derivatization may comprise a chemical addition.

These and other embodiments are described herein.

BRIEF DESCRIPTION OF THE FIGURES

The invention may be better understood by reference to the following non-limiting figures. The figures are intended to illustrate certain embodiments and/or features of the invention, and to supplement any description(s) of the invention. The figures do not limit the scope of the invention, unless the written description expressly indicates that such is the case.

FIG. 1 shows partial amino acid sequence of vWF (SEQ ID NO: 1) and A2 domain of vWF (SEQ ID NO: 2) with cleavage site for ADAMTS13 underlined and the exosite shown in italics.

FIG. 2 shows the amino acid sequence for A2 domain of vWF (SEQ ID NO: 2) with cleavage site for ADAMTS13 underlined and the exosite shown in italics.

DETAILED DESCRIPTION

The following description recites various aspects and embodiments of the present invention. No particular embodiment is intended to define the scope of the invention. Rather, the embodiments merely provide non-limiting examples of various methods and systems that are at least included within the scope of the invention. The description is to be read from the perspective of one of ordinary skill in the art; therefore, information well known to the skilled artisan is not necessarily included.

Abbreviations

Various abbreviations may be used in the application. In most, if not all, instances, the meanings of such abbreviations are known to those of skill in the art. These abbreviations include the following abbreviations, whose meanings are provided. Other abbreviations are defined herein.

Figure 3:
FIG. 3 shows the amino acid sequence of a synthetic polypeptide substrate for ADAMTS13 (SEQ ID NO: 3) based on vWF amino acid sequence, with ADAMTS13 cleavage site underlined and the exosite shown in italics and the amino acid sequence of the resultant cleavage product ("DRE peptide"; SEQ ID NO: 4).

ADAMTS13=a disintegrin and metalloproteinase with a thrombospondin type 1 motif, member 13 enzyme
DRE=a 10 amino acid polypeptide, which can be formed as a product of enzymatic cleavage of vWF73, having the sequence DREQAPNLVY (SEQ ID NO: 4); illustrated in FIG. 3.
LC=liquid chromatography
LC-MS/MS=liquid chromatography-tandem mass spectrometry
MS=mass spectrometry
MS/MS=tandem mass spectrometry
TTP=Thrombotic thrombocytopenic purpura
vWF=von Willebrand factor protein (glycoprotein)

vWF73=73 amino acid residue polypeptide (illustrated in FIG. 3) derived from the natural amino acid sequence of vWF residues Asp-1596 through Arg-1668

Definitions

The following terms, unless otherwise indicated, shall be understood to have the following meanings:

As used herein, the terms "a," "an," and "the" can refer to one or more unless specifically noted otherwise.

Throughout this application, the term "about" is used to indicate that a value includes the inherent variation of error for the device, the method being employed to determine the value, or the variation that exists among the study subjects.

As used herein, the terms "enzyme activity" or "enzymatic activity" refer to a measure of ADAMTS13 specific activity as compared to either a reference standard or a calibration curve of normal pooled plasma. The terms can be used in conjunction with the term "amount" or "level."

As used herein, the term "exosite" refers to the portion of the ADAMTS13 substrate which the enzyme recognizes to initiate cleavage. Substrates without the exosite generally will not be recognized as efficiently by the enzyme (Kokame et al., *Blood*, 2004, 103:607-612).

As used herein, the terms "subject," "individual," and "patient" are used interchangeably. The use of these terms does not imply any kind of relationship to a medical professional, such as a physician.

As used herein, the phrase "liquid chromatography" or "LC" is used to refer to a process for the separation of one or more molecules or analytes in a sample from other analytes in the sample. LC involves the slowing of one or more analytes of a fluid solution as the fluid uniformly moves through a column of a finely divided substance. The slowing results from the distribution of the components of the mixture between one or more stationery phases and the mobile phase. LC includes, for example, reverse phase liquid chromatography (RPLC) and high pressure liquid chromatography (HPLC). In some cases, LC refers to reverse phase LC with a hydrophobic stationary phase in combination with a mobile phase comprised of water and/or water-miscible organic solvents, such as methanol or acetonitrile. In some case, LC may refer to ion exchange chromatography, affinity chromatography, normal phase liquid chromatography, or hydrophilic interaction chromatography.

As used herein the term "capillary electrophoresis" (CE) refers to a process for the separation of one or more molecules or analytes in a sample from other analytes in the sample, based on their ionic mobility in an electrolyte solution while exposed to an electric field. CE includes, for example, capillary zone electrophoresis (CZE).

As used herein, the term "separate" or "purify" or the like are not used necessarily to refer to the removal of all materials other than the analyte of interest from a sample matrix. Instead, in some embodiments, the terms are used to refer to a procedure that enriches the amount of one or more analytes of interest relative to one or more other components present in the sample matrix. In some embodiments, a "separation" or "purification" may be used to remove or decrease the amount of one or more components from a sample that could interfere with the detection of the analyte, for example, by mass spectrometry.

As used herein, the term "mass spectrometry" or "MS" refers to a technique for the identification and/or quantitation of molecules in a sample. MS includes ionizing the molecules in a sample to form charged molecules (ions) in gas phase; separating the charged molecules according to their mass-to-charge ratio; and detecting the charged molecules. MS allows for both the qualitative and quantitative detection of molecules in a sample. The molecules may be ionized and detected by any suitable means known to one of skill in the art. The phrase "tandem mass spectrometry" or "MS/MS" is used herein to refer to a technique for the identification and/or quantitation of molecules in a sample, wherein multiple rounds of mass spectrometry occur, either simultaneously using more than one mass analyzer or sequentially using a single mass analyzer. As used herein, a "mass spectrometer" is an apparatus that includes a means for ionizing molecules and detecting charged molecules.

As used herein, "electrospray ionization" or "ESI" refers to a technique used in mass spectrometry to ionize molecules in a sample while avoiding fragmentation of the molecules. The sample is dispersed by the electrospray into a fine aerosol. The sample will typically be mixed with a solvent, usually a volatile organic compound (e.g., methanol or acetonitrile) mixed with water. The aerosol is then transferred to the mass spectrometer through an orifice, which can be heated to aid further solvent evaporation from the charged droplets and, ultimately, from gas-phase ions of the molecules in the sample.

As used herein, the term "stable isotopically labeled" encompasses the process of enriching a molecule with a non-radioactive isotope of a given atom so as to alter the average mass of said atom within a molecule and thereby alter the average mass of said molecule. Generally, this is accomplished by replacing the light isotopes more frequently found in nature and in natural molecules (e.g., carbon-12 or nitrogen-14), with the less common heavy isotopes (e.g., carbon-13 or nitrogen-15).

As used herein, a "quadrupole analyzer" is a type of mass analyzer used in MS. It consists of four circular rods (two pairs) that are set highly parallel to each other. The quadrupole may be in triple quadrupole format as is known in the art. The quadrupole analyzer is the component of the instrument that organizes the charged particles of the sample based on their mass-to-charge ratio. One of skill in the art would understand that use of a quadrupole analyzer can lead to increased specificity of results. One pair of rods is set at a positive electrical potential and the other set of rods is at a negative potential. To be detected, an ion must pass through the center of a trajectory path bordered and parallel to the aligned rods. When the quadrupoles are operated at a given amplitude of direct current and radio frequency voltages, only ions of a given mass-to-charge ratio will resonate and have a stable trajectory to pass through the quadrupole and be detected. As used herein, "positive ion mode" refers to a mode wherein positively charged ions are detected by the mass analyzer, and "negative ion mode" refers to a mode wherein negatively charged ions are detected by the mass analyzer. For "selected ion monitoring" or "SIM," the amplitude of the direct current and the radio frequency voltages are set to observe only a specific mass.

The term "centrifugation" refers to a process that involves the application of the centripetal force for the sedimentation of heterogeneous mixtures with a centrifuge. The increase the effective gravitational force on a sample, for example, contained in a tube, to more rapidly and completely cause the precipitate (pellet) to gather on the bottom of the tube. The remaining solution is termed "supernatant."

TTP is a known, relatively rare blood disorder, which is discussed in more detail elsewhere in this document, for example, in the section "Background of the Invention."

The terms "substrate" or "enzyme substrate" are used herein to refer to a material on which an enzyme acts.

The term "exogenous" substrate is a substrate originating from outside the sample. In certain embodiments, the "exogenous" substrate is a "synthetic" substrate.

The term "synthetic" is used here to refer to a man-made molecule, for example, produced in a laboratory or other similar facility. This will encompass both chemical synthesis as well as recombinant molecular techniques (i.e., expression from a recombinant nucleic acid construct).

The term "sequence" can be used to refer to the order of amino acids in a polypeptide, which can also be described as "primary structure," or to a polypeptide molecule, such as a polypeptide with a particular order of amino acids.

"Sequence identity" or "sequence similarity" in the context of two or more amino acid sequences, refer to two or more sequences or subsequences that are the same or have a specified percentage of amino acids that are the same (for example, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region. Various tools for measuring sequence similarity are available, such as protein BLAST available from National Center for Biotechnology Information, U.S. National Library of Medicine, Bethesda, Maryland, USA. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The terms "cleavage," "enzyme cleavage" or "enzymatic cleavage" are used herein to refer to a process or a result of enzymatic hydrolysis of a polypeptide caused by an enzyme protease (peptidase or proteinase).

The term "cleavage site" is used herein to refer to a location of cleavage by a protease in a polypeptide. The term "cleavage site" encompasses and may be used to denote "specific cleavage site," meaning a cleavage site in a polypeptide for which a protease is specific.

The term "cleavage product" is used herein to refer to a polypeptide resulting from enzymatic cleavage by a protease.

von Willebrand factor (vWf) is a large multimeric glycoprotein present in blood plasma and produced constitutively as ultra-large vWF in endothelium (in the Weibel-Palade bodies), megakaryocytes (α-granules of platelets), and subendothelial connective tissues. The basic vWF monomer is a 2050-amino acid protein containing a number of specific domains with specific functions. vWF monomers are posttranslationally N-glycosylated, arranged into dimers in the endoplasmic reticulum and into multimers in the Golgi apparatus by crosslinking of cysteine residues via disulfide bonds. vWF multimers can contain over 80 vWF monomers. vWF main known function is binding other proteins, in particular factor VIII, and it is known to be important in platelet adhesion to wound sites.

ADAMTS13 is a metalloproteinase also known as von Willebrand factor-cleaving protease (vWFCP). It is a zinc-containing metalloprotease enzyme that cleaves vWF. It is secreted in blood and degrades large vWf multimers, decreasing their activity.

Methods for Determining the Presence or Amount of ADAMTS13 Activity

The invention may be embodied in a variety of ways. In certain embodiments, the invention comprises a method to measure ADAMTS13 activity by mass spectrometry. In some embodiments tandem MS/MS is used. In some embodiments, ADAMTS13 activity is measured by LC-MS/MS. Also included are systems for measuring ADAMTS13 activity.

FIGS. 1 and 2 shows partial amino acid sequence of vWF (SEQ ID NO: 1 in FIG. 1; SEQ ID NO: 2 in FIGS. 1 and 2), with cleavage site for ADAMTS13 underlined. The methods described herein may employ a portion of the vWF A2 Domain (residues D1459-L1664) as the substrate (SEQ ID NO: 2 shown in FIG. 2 and in bold font in FIG. 1). Also shown is ADAMTS13 cleavage site (underlined) (residues 1605-1606) and the exosite (italics) (residues 1660-1668) (see FIGS. 1 and 2). FIG. 3 shows the substrate peptide having the ADAMTS13 cleavage site (underlined font) and the resultant N-terminal peptide product DREQAPNLVY (SEQ ID NO: 4) (i.e., "DRE peptide") that is a product of ADAMTS13 cleavage of the substrate polypeptide shown in FIG. 3.

Figure 4:
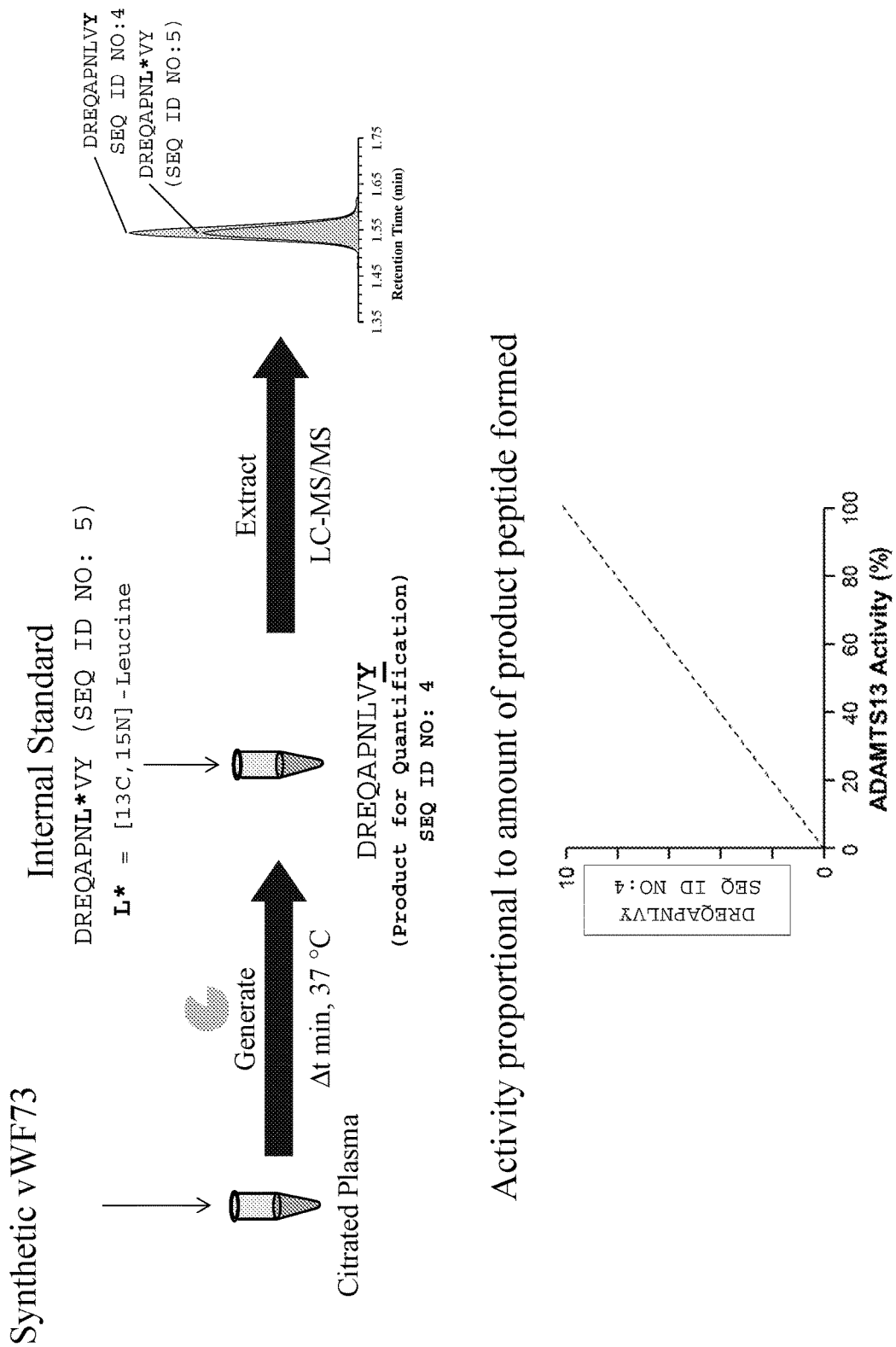
FIG. 4 shows an overview of a workflow for assay of ADAMTS13 activity by detection of the DRE peptide (SEQ ID NO: 4) by LC-MS/MS according to an embodiment of the present invention. Internal standard (SEQ ID NO:5) is also shown.

In certain embodiments, the present invention is performed as schematically illustrated in FIG. 4. An exemplary embodiment of the invention is a method for determining activity of ADAMTS13 in a sample, which may include the steps of incubating the sample with a synthetic peptide substrate for ADAMTS13 (SEQ ID NO: 3) under conditions allowing for enzymatic cleavage of the synthetic peptide substrate by ADAMTS13 to generate a DRE peptide (SEQ ID NO: 4), optionally, terminating the enzymatic cleavage in the sample being incubated; optionally, chromatographically separating the enzymatic cleavage product using liquid chromatography; and analyzing the enzymatic cleavage product by mass spectrometry to determine presence or amount of enzymatic cleavage product in the sample. The presence or the amount of the product of the enzymatic cleavage product in the sample is indicative of the presence or the amount of the activity of ADAMTS13 in the sample. As shown in FIG. 4, the method may employ an internal standard, such as DRE peptide, stable isotopically labeled with, for example, [$^{13}$C, $^{15}$N]-Leucine (SEQ ID NO:5). As is known, other types of internal standard may be employed. For example, the internal standard may be unlabeled but have a different amino acid sequence, or another amino acid in the peptide may be labeled. The internal standard, as well as the substrate peptide(s) may be made by chemical synthesis or recombinant methods.

Thus, in certain embodiments, ADAMTS13 activity may be determined by incubating a plasma sample obtained from a patient with a synthetic polypeptide substrate based on the sequence shown in FIG. 1 (SEQ ID NO: 1). The synthetic substrate may be smaller than the sequence shown in FIG. 1. In an embodiment, the synthetic substrate, termed vWF73, is a 73 amino acid residue polypeptide shown in FIG. 3 based on the partial amino acid of vWF, residues Asp-1596 through Arg-1668 (SEQ ID NO: 3). vWF73 possesses the cleavage site Tyr-1605/Met-1606. The synthetic substrate does not necessarily possess the same sequence as the sequence shown in FIG. 3 and in bold in FIG. 1; variations and modifications of the sequence are possible. In some embodiments, the substrate may have amino acid residue sequences not shown in FIG. 1 (SEQ ID NO: 1), and/or may include additional sequences such as the inclusion of an affinity tag or non-native amino acids. Examples of this might include a MYC tag (EQKLI-SEEDL—SEQ ID NO: 6), a FLAG tag (DYKDDDDK—SEQ ID NO: 7), a polyHIS tag (HHHHHH—SEQ ID NO: 8), a Glutathione S-transferase tag or a biotinylated amino acid. However, a cleavage site for ADAMTS13 is present in the synthetic substrate. In alternate embodiments, the synthetic substrate has at least 70%, 75%, 80%, 85%, 90% or 95% sequence similarity to vWF73 sequence.

Cleavage of the synthetic substrate by ADAMTS13 results in a detectable product. For example, upon cleavage of vWF73 in vitro, a 10 amino acid residue peptide is formed from the N-terminus of the substrate having the sequence DREQAPNLVY (SEQ ID NO:4), which is termed "DRE product." In an embodiment, ADAMTS13 activity is proportional to the amount of DRE product created during the incubation period. The DRE product may then be measured by mass spectrometry. In certain embodiments, the incubation may be terminated by methanol precipitation of the enzyme and the supernatant containing the DRE product may be analyzed directly using mass spectrometry. In certain embodiments, the DRE product is analyzed by liquid chromatography (LC) or another purification technique (e.g., capillary electrophoresis) coupled with tandem mass spectrometry (MS/MS) to measure the DRE-product.

The amount of ADAMTS13 activity in a sample may be determined using an internal standard. For example, using isotope dilution mass spectrometry, a stable isotope-labeled analogue of the cleavage product (for example, of DRE product) is added to the sample as an internal standard and is measured concurrently with the enzymatic cleavage product by MS or LC-MS/MS, to normalize for variation. In an embodiment, the internal standard may be added concurrently with the synthetic substrate peptide. In other embodiments, the internal standard may be added after cleavage of the synthetic substrate by ADAMTS13. In an embodiment, the measured analyte:internal standard ratio is proportional to the amount of DRE-product formed and, thereby, directly proportional to the ADAMTS13 activity. Accordingly, the measured analyte:internal standard ratio is indicative of the amount of ADAMTS13 enzymatic activity present in the sample. ADAMTS13 activity can be expressed in units of "Percent Normal Activity," with 100% Normal Activity defined, for example, by pooled plasma derived from the patients having normal ADAMTS13 activity levels.

The methods according to the embodiments of the present invention may comprise providing a sample. In this context, the term "providing" is to be construed broadly. The term is not intended to refer exclusively to a subject who provided a biological sample. For example, a technician in an off-site clinical laboratory can be said to "provide" the sample, for example, as the sample is prepared for purification by extraction and/or chromatography.

The sample is not limited to any particular sample type. The sample contains ADAMTS13, but, in general, also includes other components. In some embodiments, the sample is a sample that has been processed and prepared for purification by extraction and/or chromatography. Such processing may be useful for optimizing the effectiveness of subsequent purification steps. Such processing methods are well known to those of skill in the art.

The invention is not limited to any particular means of sample handling. In some embodiments, it may be useful to separate the sample into two or more fractions prior to partial purification by extraction and/or chromatography. In some such embodiments, two or more of such fractions may be prepared differently, for example, to help improve the sensitivity or selectivity of the separation for a particular column chemistry. In some embodiments, the method includes preparing a single sample for repeat injections across multiple liquid chromatography systems.

The invention is not limited to any particular sample size or composition. In some embodiments, the sample comprises a biological sample. In such embodiments, the sample may also include other components, such as solvents, buffers, anticlotting agents and the like. In embodiments where the sample comprises a biological sample, the biological sample can be one or more of whole blood, plasma, serum, urine, cerebrospinal fluid, tissue homogenate, saliva, amniotic fluid, bile, mucus, peritoneal fluid, or lymphatic fluid. The invention is not limited to any particular volume of biological sample. In some embodiments, the biological sample is at least about 0.5-250 µL, at least about 1-100 µL, or at least about 2-50 µL in volume. In certain embodiments, the biological sample is at least about 2-50 µL in volume.

Termination of the enzymatic cleavage in the sample being incubated is not limited to any particular method. In some embodiments, termination of the enzymatic cleavage by ADAMTS13 in the sample is accomplished by adding a precipitating reagent to the sample after the appropriate incubation period, in an amount sufficient to terminate ADAMTS13 enzymatic reaction. A precipitating reagent can be methanol, acetonitrile, acetone, 2-propanol, ammonium sulfate, trichloroacetic acid or perchloric acid. In some embodiments, temperature may be used to effectively terminate the reaction. The sample may be heated so as to inactivate the ADAMTS13 or the sample may be cooled, potentially frozen, to slow the reaction to an effective stop. In some embodiments, the reaction may be stopped by adjusting the sample pH not conducive for ADAMTS13 activity, for example, below about pH 3 or above about pH 9. In other embodiments, the reaction may be stopped by adding inhibitors of ADAMTS13, such as EDTA or other protease inhibitors. In some embodiments, it may not be necessary to terminate the enzymatic reaction. For example, ADAMTS13 enzymatic reaction may be continuously monitored during the incubation step by repeated sampling over the course of time, rather than measurement at a single time point.

Partial purification of the sample provides a partially purified sample. Partial purification can be conducted at various stages of the method. For example, in some embodiments, partial purification can be conducted after incubation of the sample and termination of ADAMTS13 activity, resulting in a sample comprising ADAMTS13 enzymatic cleavage product. In some other embodiments, partial purification can be conducted prior to the incubation step. More than one partial purification step may be used in the methods according to the embodiments of the present invention. Partial purification is not limited by the method or the result of the partial purification. In some embodiments, the concentrations of one or more of the various components in the sample, other than the component of interest, have been reduced. For example, concentration of the other components may be reduced relative to the concentration of enzymatic cleavage product in the partially purified sample. In another example, concentration of the other components may be reduced relative to the concentration of ADAMTS13 in the partially purified sample.

Thus, the term "removing" or "removal" does not necessarily imply the complete removal of a component. Some amount of the removed component can still be present in the partially purified sample, although its concentration relative to that of the component of interest will be lower than in the pre-extraction sample. In some embodiments, the relative concentration of the removed component to that of enzymatic cleavage product in the partially purified sample is no more than 90%, or no more than 75%, or no more than 50%, or no more than 33%, or no more than 25%, or no more than 10% or no more than 5%, or no more than 1%, of its relative concentration to enzymatic cleavage product in the sample prior to the partial purification step. The invention is not limited to any particular type of removed component. In some embodiments, one or more of the removed components is a compound that can interfere with the analysis by mass spectrometry or with liquid chromatography. One example of partial purification method is centrifugation after the termination of the reaction by addition of an organic solvent. During the centrifugation, the precipitated components of thus treated sample are removed, while the supernatant is further purified and/or analyzed.

In some embodiments of the invention, the partially purified sample can undergo one or more processing steps before chromatographic separation. For example, in some embodiments, the partially purified sample is evaporated. Then, the resulting residue is reconstituted in a solvent system. Any suitable solvent system can be used for reconstituting the residue. In some embodiments, the solvent system is a solvent system that is compatible with chromatographic separation. In some embodiments, the solvent system for reconstitution includes, but is not limited to, water, methanol or mixtures thereof. In some other embodiments, the partially purified sample may undergo a chemical or enzymatic treatment so as to modify the enzymatic cleavage product. For example, the cleavage product may be chemically derivatized or further hydrolyzed. In some embodiments, the cleavage product may be further hydrolyzed with other enzymes.

In some embodiments, the methods include (comprise) a step of chromatographically separating polypeptide enzymatic cleavage product, for example, DRE product, using liquid chromatography. The invention is not limited to any particular manner of performing liquid chromatography. In general, the chromatographic separation step includes using at least one liquid chromatography (LC) column. In some embodiments, multiple LC columns are used, such as two or more, or three or more, or four or more LC columns. In some such embodiments two, three, four, five, six, eight or ten LC columns are used. In some such embodiments, two or more of these LC columns are arranged parallel to each other and are connected inline to the same mass spectrometer.

The invention is not limited to any particular types of columns. Any column suitable for the separation of enzymatic cleavage product can be used. In some embodiments, one or more analytical columns are used. In some embodiments, the column is a C18 column, but could be comprised of C12, C8, C4, Phenyl-hexyl, amide, amine, or PFP.

Further, the invention is not limited to any particular mobile phase. Any suitable mobile phase can be used, as long as the mobile phase is suitable for use with a particular LC column and for chromatographically separating enzymatic cleavage product in the LC column. In some embodiments, the mobile phase is comprised of acetonitrile (0-100%). Or, the mobile phase may be comprised of methanol (0-100%). In some such embodiments, the mobile phase employs a gradient, such that the relative ratios of two or more solvents are varied over time. In some embodiments, the mobile phase is comprised of ion pairing reagents, such as trifluoroacetic acid, formic acid, ammonium, heptafluorobutyric acid, and/or acetic acid.

In certain embodiments, two or more LC columns can be used in parallel and connected inline to the same mass spectrometer, e.g., to improve throughput. In some such embodiments, a sample (which can be a partially purified sample) is introduced to the two or more LC columns at different times. In some embodiments, the introduction of the test sample to the two or more LC columns is staggered, meaning that there is a pre-determined time interval separating the introduction of sample to two or more LC columns. Appropriate time intervals can be selected based on various factors, including the elution time, column chemistries and the potential need to avoid interfering with the analysis of the enzymatic cleavage product eluted from one or more of the other LC columns.

In some embodiments of the invention, an LC column can be placed in series with another column. For example, in some embodiments, suitable guard columns can be employed. Those of skill in the art are able to select appropriate guard columns for use in the present methods. In some embodiments, a guard column is placed in parallel with another LC column. Such series of two or more columns can also be arranged in parallel, such that there are two or more series of columns operating in parallel, where each series contains two or more columns. In other embodiments, online extraction columns may be employed. For example, online solid phase extraction columns may be used in some embodiments of the method.

In some embodiments of the invention, the enzymatic cleavage product may be purified by electrophoresis. For example, in some embodiments, the enzymatic cleavage product is separated from potentially interfering substances using capillary electrophoresis.

In some embodiments, the methods comprise analyzing the purified or separated enzymatic cleavage product by mass spectrometry to determine the presence or amount of the enzymatic cleavage product. In some embodiments, two or more of the LC columns feed into the same mass spectrometer. In some further embodiments, three or more of the LC columns feed into the same mass spectrometer. In some embodiments, the mass spectrometer is part of a combined LC-MS system.

The invention is not limited to any particular type of mass spectrometer. Any suitable mass spectrometer can be used. In some embodiments, the method employs a tandem mass spectrometer. In some such embodiments, analyzing enzymatic cleavage product can include, ionizing enzymatic cleavage product, analyzing the ionized enzymatic cleavage product, fragmenting the enzymatic cleavage product ion into two or more fragment ions, and analyzing the fragment ions.

The invention is not limited to a mass spectrometer using any particular ionization methods. The method may utilize ionization techniques suitable to the generation of multiply charged ions from the enzymatic cleavage product. Suitable ionization methods include, but are not limited to photoionization, electrospray ionization, atmospheric pressure chemical ionization, and electron capture ionization. And in embodiments that employ fragmenting, any suitable fragmentation technique can be used. Suitable techniques include, but are not limited to collision induced dissociation, electron capture dissociation, electron transfer dissociation, infrared multiphoton dissociation, radiative dissociation, electron-detachment dissociation, and surface-induced dissociation.

In some embodiments, the tandem mass spectrometer is a MDS-Sciex API5500 triple quadrupole mass spectrometer. In some embodiments, the tandem mass spectrometer has an atmospheric pressure ionization source, and the analyzing step comprises an ionization method selected from the group consisting of photoionization, electrospray ionization (ESI), atmospheric pressure chemical ionization (APCI), electron capture ionization, electron ionization, fast atom bombardment/liquid secondary ionization (FAB/LSI), field ionization, field desorption, thermospray/plasmaspray ionization, particle beam ionization, and so-called "hybrid ionization" techniques, such as laser ablation electrospray ionization (LAESI), desorption electrospray ionization (DESI) or matrix assisted laser desorption electrospray ionization (MALDESI). The ionization method may be in positive ion mode or negative ion mode. The analyzing step may also include multiple reaction monitoring (MRM, also referred to as selected reaction monitoring or SRM) or selected ion monitoring (SIM), and the two or more biomolecules are analyzed simultaneously or sequentially. In some embodiments, the analyzing step uses a quadrupole analyzer. In some embodiments, the mass spectrometer is a triple quadrupole mass spectrometer. In some embodiments, the analyzing step may be performed with product ion scanning on quadrupole-time-of-flight (Q-TOF) or quadrupole-orbitrap instrument, such as in parallel reaction monitoring (PRM).

The methods, in some embodiments, include using an internal standard. In such embodiments, the internal standard can be introduced at any suitable point prior to the ionization step. Any suitable internal standard can be used. In some embodiments, the internal standard is stable isotopically-labeled equivalent of the enzymatic cleavage product. In some such embodiments, the internal standard is labeled by stable isotopic enrichment of one or more amino acids. For example, in some embodiments the internal standard is the DRE peptide having [$^{13}C$, $^{15}N$]-Leucine. Or, other isotopes used and/or amino acids may be labeled.

In some embodiments, the amount of ADAMTS13 enzymatic activity in the sample need not be quantified. In some embodiments, the method can be used to determine the presence or absence of ADAMTS13 enzymatic activity in a sample. In other embodiments, the method is used to determine the amount of ADAMTS13 enzymatic activity in a sample. For example, in some embodiments and/or aspects, the invention provides methods for determining an amount of ADAMTS13 activity in a sample, comprising the steps of incubating the sample with a synthetic peptide substrate for ADAMTS13 (and an internal standard) under conditions allowing for enzymatic cleavage of the synthetic peptide substrate by ADAMTS13, optionally terminating the enzymatic cleavage in the sample being incubated, optionally chromatographically separating an enzymatic cleavage product and the internal standard from other components of the sample using liquid chromatography, and ionizing the enzymatic cleavage product and the internal standard to generate multiply charged ions that are analyzed by mass spectrometry to determine the amount of enzymatic cleavage product and the internal standard in the sample, wherein a ratio of the determined amounts of the enzymatic cleavage product and the internal standard is indicative of the amount of activity of ADAMTS13 in the sample.

In some embodiments, the method is not limited by any lower-limit of quantification (LLOQ) and/or upper-limit of quantification (ULOQ). In some embodiments, the LLOQ is 2% and the ULOQ is 100%.

The amount of activity in the sample may be determined by comparison to an external standard curve. For example, the quantity of DRE peptide may be compared to an external standard curve of calibration standard generated using pooled normal plasma having approximately 100% ADAMTS13 that is serial diluted (e.g., to 2% ADAMTS13 activity). The method is not limited to a specific number of calibration levels. In some embodiments, only a single point is need to generate the calibration curve. In some embodiments, the calibrator may added into the sample.

Methods of Generating Reports

In at least one aspect, the invention provides methods for generating a report for diagnosing a disease or condition associated with reduced activity of ADAMTS13 in a subject. One example of such disease or condition is TTP. Such a method may include the steps of incubating the sample with a synthetic peptide substrate for ADAMTS13 and an internal standard product peptide under conditions allowing for enzymatic cleavage of the synthetic peptide substrate by ADAMTS13, optionally terminating the enzymatic cleavage in the sample being incubated, optionally chromatographically separating an enzymatic cleavage product and the internal standard from other components of the sample using liquid chromatography, ionizing the enzymatic cleavage product and the internal standard to generate multiply charged ions that are analyzed by mass spectrometry to determine the amount of enzymatic cleavage product and the internal standard in the sample, wherein a ratio of the determined amounts of the enzymatic cleavage product and the internal standard is indicative of the amount of activity of ADAMTS13 in the sample, and generating a report that recites the amount of activity of ADAMTS13 in the sample.

Based on the information on the amount of activity of ADAMTS13 in the sample, one could assess whether a subject has an abnormally low amount of such activity. Such information can be useful for diagnosing one or more diseases or disorders that may be associated with aberrant levels of ADAMTS13 activity in a subject. The features and embodiments of all steps except the steps of generating the report are described immediately above. As noted above, the method can employ more than one column, e.g., two or more columns in parallel connected inline to the same mass spectrometer.

In an embodiment, an ADAMTS13 activity level below 10% is highly indicative of thrombotic thrombocytopenic purpura (TTP), but in certain embodiments should not be used as the sole diagnostic procedure without confirmation of the diagnosis by another medically established diagnostic product or procedure. Conversely, an ADAMTS13 activity level greater than 10% may not completely exclude clinical diagnosis of TTP. As many as 40% of patients with clinically diagnosed TTP have ADAMTS13 levels greater than 10%. Other conditions that could have normal or mild to moderate deficiency of ADAMTS13 activity include hemolytic uremic syndrome (HUS), atypical hemolytic uremic syndrome (aHUS), and other thrombotic microangiopathies associated with hematopoietic stem cell and solid organ transplantation, liver disease, DIC, sepsis, pregnancy or effects of certain medications (e.g., ticlopidine, clopidogrel, cyclosporine, mitomycin C, quinine).

In some embodiments, an ADAMTS13 activity measurement may be used to determine the presence and/or amount of ADAMTS13 inhibitor in the sample. By mixing at a known ratio a sample with known low activity with a sample with known normal activity, the activity of the resulting mixed sample may be measured. Based on the known ratio of the mixture and known activity of the individual samples, one can compare the measured activity in the mixture to the expected activity in the mixture, whereby a measured activity lower than the expected activity is indicative of the presence and amount of inhibitor in the low activity sample. In some instances, the low activity sample may be heat inactivated.

Systems

In another aspect, the invention provides systems for determining the presence or amount of ADAMTS13 activity in a sample. For example, a system comprises a station for incubating the sample with a synthetic peptide substrate for ADAMTS13 under conditions allowing for enzymatic cleavage of the synthetic peptide substrate by ADAMTS13, and a station for multiply charging (i.e., ionizing) and analyzing the enzymatic cleavage product by mass spectrometry to determine the amount of the enzymatic cleavage product in the sample, wherein the amount of the enzymatic cleavage product is indicative of the activity of ADAMTS13 in the sample. The system may also comprise a station for chromatographically separating an enzymatic cleavage product using liquid chromatography or other separation methods (e.g., capillary electrophoresis).

Such systems can include various embodiments and sub-embodiments analogous to those described above for methods according to the embodiments of the present invention. These systems include various stations. As used herein, the term "station" is broadly defined and includes any suitable apparatus or collections of apparatuses suitable for carrying out the recited method. The stations need not be integrally connected or situated with respect to each other in any particular way. The invention includes any suitable arrangements of the stations with respect to each other. For example, the stations need not even be in the same room. But in some embodiments, the stations are connected to each other in an integral unit.

The methods and systems according to the embodiments of the present invention possess various advantages. For example, the use of LC-MS/MS in the methods and systems of the present invention is particularly advantageous. Previous assays of ADAMTS13 have employed either immunoassay procedures (Kato et al., 2006, *Transfusion* 46:1444-1452), fluorescence resonance energy transfer (FRET) (Kokame et al., *Br. J. Hematol.*, 2005, 129:93-100, or (SELDI-TOF)-mass spectrometry (Jin et al., *J. Thrombosis and Haemostasis*, 2006, 4:333-338). The methods and systems described herein provide increased sensitivity (e.g., LLOQ of 2%), and specificity as compared to immunoassay, increased throughput and reduced cost as compared to FRET, and increased specificity due to the generation of multiply-charged ions by electrospray ionization, which facilitates analysis by tandem mass spectrometry as compared e.g., to (SELDI-TOF)-MS.

NON-LIMITING EMBODIMENTS

Non-limiting embodiments include:

1. A method for determining a disintegrin and metalloproteinase with a thrombospondin type 1 motif, member 13 (ADAMTS13) enzyme activity in a sample, comprising:

(a) incubating the sample with an exogenous peptide substrate for ADAMTS13 under conditions allowing for enzymatic cleavage of the exogenous peptide substrate by ADAMTS13 to produce an enzymatic cleavage product;

(b) ionizing the enzymatic cleavage product to generate a multiply charged gas-phase ion of said cleavage product; and, (c) analyzing said multiply charged gas-phase ion by mass spectrometry to determine the presence or amount of enzymatic cleavage product in the sample, wherein the presence or the amount of the product of the enzymatic cleavage product in the sample is indicative of the presence or the amount of the activity of ADAMTS13 in the sample.

2. The method of paragraph 1, further comprising, after step (a) but prior to step (b), a step of partially purifying the enzymatic cleavage product, and wherein step (b) is performed on the partially purified enzymatic cleavage product.

3. The method of paragraph 2, wherein the step of partially purifying the enzymatic cleavage product comprises centrifugation, and wherein step (b) is performed on a supernatant comprising the enzymatic cleavage product.

4. The method of paragraph 2, wherein the step of partially purifying the enzymatic cleavage product comprises liquid chromatography to generate an eluent comprising the enzymatic cleavage product, and wherein step (b) is performed on the eluent.

5. The method of paragraph 2, wherein the step of partially purifying the enzymatic cleavage product comprises capillary electrophoresis to generate an eluent comprising the enzymatic cleavage product, and wherein step (b) is performed on the eluent.

6. The method of paragraph 2, wherein the step of partially purifying the enzymatic cleavage product comprises solid phase extraction to generate an eluent comprising the enzymatic cleavage product, and wherein step (b) is performed on the eluent.

7. The method of paragraph 2, wherein the step of partially purifying the enzymatic cleavage product comprises filtration to generate an eluent comprising the enzymatic cleavage product, and wherein step (b) is performed on the eluent.

8. The method of paragraph 2, wherein the step of partially purifying the enzymatic cleavage product comprises filtration to generate a retained fraction comprising the enzymatic cleavage product, and wherein step (b) is performed on the retained fraction.

9. The method of paragraph 2, wherein the step of partially purifying the enzymatic cleavage product comprises the use of affinity enrichment of the enzymatic cleavage product, and wherein step (b) is performed on the affinity enriched enzymatic cleavage product.

10. The method of paragraph 9, wherein the affinity enrichment technique uses an immobilized meatal affinity resin.

11. The method of paragraph 9, wherein the affinity enrichment technique utilizes an antibody.

12. The method of paragraph 9, wherein the affinity enrichment technique utilizes a fragment of an antibody, such as a Fab fragment.

13. The method of paragraph 9, wherein the affinity enrichment technique utilizes streptavidin.

14. The method of paragraph 9, wherein the affinity enrichment technique utilizes protein-G.

15. The method of paragraph 9, wherein the affinity enrichment technique utilizes protein-A.

16. The method of paragraph 9, wherein the affinity enrichment technique utilizes an aptamer 17. The method of paragraph 1, further comprising, between step (a) and (b), and optionally prior to the partial purification step of paragraph 2, a step of terminating the enzymatic cleavage in the sample being incubated.

18. The method of paragraph 17, wherein the terminating step comprises adding a precipitating reagent to the sample being incubated.

19. The method of paragraph 18, wherein the precipitating reagent comprises methanol.

20. The method of paragraph 18, wherein the precipitating reagent comprises acetonitrile.

21. The method of paragraph 18, wherein the precipitating reagent comprises acetone.

22. The method of paragraph 18, wherein the precipitating reagent comprises 2-propanol 23. The method of paragraph 18, wherein the precipitating reagent comprises sulfate.

24. The method of paragraph 18, wherein the precipitating reagent comprises trichloroacetic acid 25. The method of paragraph 18, wherein the precipitating reagent comprises perchloric acid 26. The method of paragraph 17, wherein the terminating step comprises adjusting the pH of the sample being incubated below pH 5.

27. The method of paragraph 17, wherein the terminating step comprises adjusting the pH of the sample being incubated above pH 9.

28. The method of paragraph 17, wherein the terminating step comprises heating the sample being incubated to a temperature above 50 degrees centigrade.

29. The method of paragraph 17, wherein the terminating step comprises cooling the sample being incubated to a temperature below 15 degrees centigrade.

30. The method of paragraph 17, wherein the terminating step comprises adding an inhibitor of ADAMTS13 to the sample being incubated.

31. The method of paragraph 30, wherein the inhibitor is ethylenediaminetetraacetic acid.

32. The method of paragraph 1, wherein the exogenous substrate is a synthetic peptide having at least 70% sequence similarity to amino acid sequence of vWF73.

33. The method of paragraph 1, wherein the exogenous peptide substrate has at least 70% sequence similarity to von Willebrand Factor sequence.

34. The method of paragraph 1, wherein the exogenous peptide substrate comprises a cleavage site for ADAMTS13.

35. The method of paragraph 1, wherein the synthetic peptide substrate comprises one or more affinity tags.

36. The method of paragraph 35, wherein the one or more affinity tags are selected from the group consisting of: MYC-tag, FLAG-tag, polyHis-tag and GST-tag.

37. The method of paragraph 35, wherein the one or more affinity tags contain the epitope for an antibody.

38. The method of paragraph 1, wherein the exogenous peptide substrate comprises one or more non-natural amino acids.

39. The method of paragraph 38, wherein the one or more non-natural amino acids are biotinylated.

40. The method of paragraph 38, wherein the one or more non-natural amino acids are stable isotopically labeled amino acids.

41. The method of paragraph 1, wherein the enzymatic cleavage product comprises a polypeptide having a sequence of DREQAPNLVY.

42. The method of paragraph 1, wherein step (b) includes ionizing the enzymatic cleavage product using an ionization technique selected from the group consisting of electrospray ionization, atmospheric pressure chemical ionization and atmospheric pressure photoionization.

43. The method of paragraph 1, wherein the analyzing step (c) uses tandem mass spectrometry 44. The method of paragraph 1, wherein the analyzing step (c) uses ions having a m/z selected from the group consisting of 602.8±2, 182.1±2, 281.1±2, 462.7±2, 512.3±2, 600.3±2, 605.3±2, 811.4±2, 924.5±2 and 1023.5±2.

45. The method of paragraph 1, wherein the analyzing step (c) includes determining the specific activity of the ADAMTS13.

46. The method of paragraph 1, wherein an internal standard is added prior to the ionization step (b).

47. The method of paragraph 46, wherein the internal standard is added concurrently with the substrate.

48. The method of paragraph 46, wherein the internal standard is added to the sample prior to the incubation step (a).

49. The method of paragraph 46, wherein the internal standard is added to the sample being incubated.

50. The method of paragraph 46, where the internal standard is an isotopically labelled equivalent of the enzymatic cleavage product.

51. The method of paragraph 46, wherein the presence or amount of the internal standard is determined along with the presence or amount of the enzymatic cleavage product in step (c).

52. The method of paragraph 51, wherein the ratio between the determined amount of the internal standard and the determined amount of the enzymatic cleavage product is indicative of the amount of the enzymatic cleavage product formed in step (a).

53. The method of paragraph 51, wherein the ratio between the determined amount of the internal standard and the determined amount of the enzymatic cleavage product is indicative of the amount of activity of ADAMTS13 in the sample.

54. The method of paragraph 1, wherein the sample is a biological fluid obtained from a patient.

55. The method of paragraph 54, wherein the biological fluid is plasma.

56. The method of paragraph 54, wherein the biological fluid is serum.

57. The method of any one of paragraphs 1, 2 and 17, further comprising, between steps (a) and (b), and optionally either before or after the partial purification step, but after the termination step, a step of modifying the molecular structure of the enzymatic cleavage in the sample being incubated.

58. The method of paragraph 57, wherein the modifying step comprises further hydrolyzing the enzymatic cleavage product.

59. The method of paragraph 58, wherein the hydrolysis is performed using an enzyme.

60. The method of paragraph 59, wherein the enzyme is trypsin.

61. The method of paragraph 59, wherein the enzyme is pepsin.

62. The method of paragraph 59, wherein the enzyme is LysC.

63. The method of paragraph 59, wherein the hydrolysis is performed using a chemical reagent.

64. The method of paragraph 63, wherein the chemical reagent is formic acid.

65. The method of paragraph 63, wherein the chemical reagent is cyanogen bromide.

66. The method of paragraph 57, wherein the enzymatic cleavage product is derivatized.

67. The method of paragraph 66, wherein the derivatization is enzymatically catalyzed.

68. The method of paragraph 66, wherein the derivatization is chemical addition.

69. A method for determining an amount of activity of enzyme disintegrin and metalloproteinase with a thrombospondin type 1 motif, member 13 (ADAMTS13) in a sample, comprising:
(a) incubating the sample with a synthetic peptide substrate for ADAMTS13 and an isotopically labelled equivalent of a product peptide to the sample under conditions allowing for enzymatic cleavage of the synthetic peptide substrate by ADAMTS13;

(b) terminating the enzymatic cleavage in the sample being incubated;

(c) partially purifying an enzymatic cleavage product and the internal standard from other components of the sample using liquid chromatography or another purification technique; and, (d) analyzing the partially purified enzymatic cleavage product and the standard by mass spectrometry to determine the amount of enzymatic cleavage product and the internal standard in the sample, wherein a ratio of the determined amounts of the enzymatic cleavage product and the internal standard is indicative of the amount of activity of ADAMTS13 in the sample.

70. A method of generating a report useful for diagnosing a disease or condition associated with reduced activity of enzyme disintegrin and metalloproteinase with a thrombospondin type 1 motif, member 13 (ADAMTS13) in a sample obtained from a patient, the method comprising performing any of the methods of any of the above paragraphs and generating a report that recites the amount of activity of ADAMTS13 in the sample.

71. The method of paragraph 70, wherein the disease or the condition is thrombotic thrombocytopenic purpura.

72. A method for diagnosing thrombotic thrombocytopenic purpura in a subject, comprising performing any of the methods of any of the above paragraphs, wherein an ADAMTS13 activity level below 10% normal values is highly indicative of thrombotic thrombocytopenic purpura (TTP).

73. A system for determining activity of enzyme disintegrin and metalloproteinase with a thrombospondin type 1 motif, member 13 (ADAMTS13) in a sample, the system comprising:

(a) a station for incubating the sample with an exogenous peptide substrate for ADAMTS13 under conditions allowing for enzymatic cleavage of the exogenous peptide substrate by ADAMTS13 to generate an enzymatic cleavage product;

(b) a station for ionizing the enzymatic cleavage product to generate a multiply charged gas-phase ion of said cleavage product; and, (c) a station for analyzing the multiply charged gas phase ion by mass spectrometry to determine the presence and/or amount of the enzymatic cleavage product in the sample, wherein the amount of the enzymatic cleavage product is indicative of the activity of ADAMTS13 in the sample.

74. The system of paragraph 73, further comprising a station for chromatographically separating the enzymatic cleavage product using liquid chromatography.

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter.

EXAMPLE

ADAMTS13 activity is determined by incubating patient plasma with a synthetic substrate under optimized (i.e., non-physiological) conditions. The synthetic substrate, termed vWF73, is a 73 amino acid residue peptide derived from the natural amino acid sequence of vWF residues Aspartic acid-1596 through Arginine-1668 and, thereby, possesses the ADAMTS13 cleavage site (Tyrosine-1605/Methionine-1606). Upon cleavage of vWF73 in vitro, a 10 amino acid residue product peptide is formed from the N-terminus of the substrate, the product peptide having the sequence DREQAPNLVY (SEQ ID NO:4). ADAMTS13 activity is proportional to the amount of product peptide created during a 30 min incubation, which is measured by isotope dilution following methanol precipitation using liquid chromatography (LC) coupled with tandem mass spectrometry (MS/MS). The assay is externally calibrated using pooled plasma derived from clinically normal individuals and standardized against the WHO 1st International Standard for ADAMTS13 in Plasma (12/252). The standardized ADAMTS13 activity, expressed in units of "percent normal activity," is interpolated from the external calibration curve created from dilution of the pooled normal plasma using with a synthetic matrix to span 2 to 100% normal activity.

Specimens

A recommended sample is 0.1-0.8 mL serum or plasma dispensed in buffered sodium citrate. About 10-20 µL is used for each assay. Serum collected using standard sampling tubes or tubes containing separating gel. Serum/Plasma should be removed from the cells within one hour of collection and transferred to a plastic transport tube. Serum and plasma should be stored frozen at −20° C. until used.

Reagent Preparation

For the ADAMTS13 assay, Generation Buffer (10 mM Bis-Tris, 10 mM Calcium chloride, pH 6.0) is used.

A stock solution of the DRE peptide at 50 µg/mL and Internal Standard (IS), NH2-DREQAPNL*VY-OH (SEQ ID NO: 5) L*=[$^{15}$N, $^{13}$C6]-Leucine) (SIL.vWF10) is made by adding 1 mL of 0.001% Zwittergent 3-16 directly to a single 0.05 mg vial of NAT.vWF10 or SIL.vWF10 to produce 50 µg/mL concentration. The solution is mixed and kept at room temperature for at least 15 min prior to use. The solution is used within 2 hours or frozen and is stable at <−70° C. for up to 2 years.

A stock substrate solution of the substrate peptide (vWF73) is purchased directly from the manufacturer in 30% acetonitrile, 0.1% formic acid with a concentration assignment by amino acid analysis (typically, 100 to 1000 µmon). The stock substrate can be stored at <−70° C. for up to 2 years.

The sequence of vWF73 is shown below and in FIGS. 1-3.

(SEQ ID NO: 3)
NH2-DREQAPNLVYNIVTGNPASDEIKRLPGDIQVVPIGVG

PNANVQELERIGWPNAPILIQDFETLPREAPDLVLQR-OH.

A Working Substrate-Internal Standard Mixture (900 nmol/L vWF73, 50 ng/mL) (SIL.vWF10) is made by appropriately diluting the stock solutions into 0.001% Zwittergent 3 16. It is stored at <−70° C. for up to 3 months. The aliquots are discarded after 2 freeze/thaws.

A Working System Suitability Test Solution (10 ng/mL NAT.vWF10) in 0.001% Zwittergent 3-16 is made. It is stored at <−70° C. for up to 2 years.

A Blank Matrix (60 mg/mL BSA in PBS) is made.

Pooled Normal Plasma (PNP) is used to generate low and mid quality cut-off controls. To make the PNP, five replicate specimens from 20 ostensibly normal individuals are collected into 3.2% Sodium citrate tubes (a total of 100 specimens). The specimens are processed per normal procedure, discarding any hemolyzed specimens, pooled and used immediately or frozen. They are stored at <−70° C. for up to 2 months. To prepare Heat Inactivated Pooled Normal Plasma (HIPNP), 10 to 50 mL aliquots of PNP are incubated for 12 to 16 hours at 56° C. in a water bath. The HIPNP may be stored refrigerated (2-8° C.) for up to 1 week or at <−10° C. for up to 1 year.

Calibration and Reference Standards

The quantity of DRE peptide is compared to an external standard curve of calibration standard generated using PNP having 100% ADAMTS13 that is serial diluted to 2% ADAMTS13 Activity. An acceptable calibration curve fitting is defined as being between 85 and 115% throughout the range. Additional standardization employs the WHO 1$^{st}$ International Standard for ADAMTS13 in plasma as a reference standard, which, when undiluted, exhibits 91.0% activity. The mean recovery for the reference standard should be between 90 and 110%. The reference standard recovery is used to adjust the calibrator values accordingly. For example, if the reference standard recovery is 112.3%, than the assigned valued for a 20% calibrator would be 17.81% (20%/1.123).

Matrix Controls

The following matrix controls (QCs) are prepared in pooled normal plasma (PNP). The lot of PNP used in preparation of the QCs should differ from the lot of PNP used in working calibrators.

Low QC is made by diluting PNP with HI-PNP to have a mean ADAMTS13 activity between 5-15% of normal (i.e., PNP). Mid QC is made by adding ADAMTS13 antibody into PNP to create about a 1:50 antibody mixture, then diluting (with additional PNP) to identify a dilution with between 20-40% ADAMTS13 activity.

ADAMTS13 Assay Procedure

A water bath is preheated to 45° C. (±3° C.), and blanks, standards, controls, samples, and frozen reagents are thawed under ambient conditions. Aliquots of 13 μL of the blanks, standards, controls and samples are pipetted into separate wells of a 1.2-mL, 96 deep well plate, (Plate A). Next, aliquots of 923 μL of Generation Buffer are pipetted into each well of Plate A. The plate is then sealed (e.g., with foil) and vortexed to mix the reagents.

At this point, an aliquot (25 μL) of Working Substrate/Internal Standard Mixture is added into matching wells of a new 1.2-mL, 96 deep well plate (i.e., Plate B). Both plates include wells for the double blank (0.001% Zwittergent 3-16). At this point, 25 μL of diluted samples from Plate A are transferred to the Working Substrate/Internal Standards in Plate B. Plate B is then sealed (e.g., with an adhesive sealant) and subjected to centrifugation and vortexing to ensure complete transfer and mixing. Plate B is then incubated in a 45° C. (±3° C.) water bath for 30 min (±1 min). Plate B is then centrifuged and 250 μL of methanol added to each well to terminate the reaction.

At this point the samples are ready for LC/MS-MS analysis. After sealing the wells (e.g., with foil) the samples (i.e., Plate B) are vortexed (5 min) and centrifuges (e.g., 10 min at about 3250 rpm). Aliquots of each sample (200 μL) of supernatant are then transferred from Plate B to a new plate, Plate C. After sealing (e.g., with foil), the samples are cooled and subjected to LC-MS/MS. LC employs a reverse phase C18 stationary phase with an acetonitrile gradient. The loading includes a second pump to apply additional aqueous reagent to improve loading. DMSO may be included in the acetonitrile gradient. MS/MS employs two qualifiers (i.e., additional fragments) to ensure the quantifier signal is not compromised by a contaminant(s), as shown in Table 1.

TABLE 1

Analyte and internal standard detection

| Analyte/Internal Standard | Quantifier | Qualifier A | Qualifier B |
|---|---|---|---|
| Analyte Name | ADAMTS13 Activity | ADAMTS13 qual-A | ADAMTS13 qual-B |
| Analyte Transitions (m/z) | 602.801/924.453 | 602.801/811.369 | 602.801/512.265 |
| Internal Standard Name | IS | IS qual-A | IS qual-B |
| Internal Standard Transitions | 606.310/931.471 | 606.310/811.369 | 606.310/515.773 |

Analytical Measurable Range

The lower (LLOQ) and upper (ULOQ) limit of quantification as determined in validation are listed below in Table 2.

TABLE 2

Limits of quantification

| LLOQ | ULOQ |
|---|---|
| 2% | 100% |

Clinically Reportable Range

The lower (LRL0 and upper (URL) reportable limits as determined in validation are listed below in Table 3.

TABLE 3

Reportable limits

| LRL | URL |
|---|---|
| 2% | 1000% |

Reference Interval & Interpretation

The normal reference interval established during validation of the assay to be: >66% Normal ADAMTS13 Activity. Levels less than 66% are suggestive of an underlying condition.

While the preferred embodiments of the invention have been illustrated and described, it will be appreciated that various changes can be made therein without departing from the spirit and scope of the invention. All printed patents and publications referred to in this application are hereby incorporated herein in their entirety by this reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1215802 ADAMTS13Untitled_ST25_2.txt, created on Nov. 6, 2020 and having a size of 22 kilobytes. The sequence listing contained in this ASCII formatted document is part of the specification and is herein incorporated by reference in its entirety.

We claim:
1. A method for determining a disintegrin and metalloproteinase with a thrombospondin type 1 motif, member 13 (ADAMTS13) enzyme activity in a sample, comprising:
(a) incubating the sample with an exogenous peptide substrate for ADAMTS13 under conditions allowing for enzymatic cleavage of the exogenous peptide substrate by ADAMTS13 to produce an enzymatic cleavage product, wherein the exogenous peptide substrate comprises an ADAMTS13 cleavage site, and wherein the enzymatic cleavage product comprises a sequence with at least 70% sequence identity to SEQ ID NO:4;
(b) ionizing the enzymatic cleavage product to generate a multiply charged gas-phase ion of the enzymatic cleavage product; and,
(c) analyzing the multiply charged gas-phase ion by tandem mass spectrometry to determine presence or amount of enzymatic cleavage product in the sample, wherein the presence or the amount of the enzymatic cleavage product in the sample is indicative of presence or amount of enzyme activity of ADAMTS13 in the sample.

2. The method of claim 1, further comprising, after step (a) but prior to step (b), a step of partially purifying the enzymatic cleavage product, wherein step (b) is performed on partially purified enzymatic cleavage product.

3. The method of claim 2, wherein the step of partially purifying the enzymatic cleavage product comprises centrifugation, and wherein step (b) is performed on a supernatant comprising the enzymatic cleavage product.

4. The method of claim 2, wherein the step of partially purifying the enzymatic cleavage product comprises one or more of liquid chromatography, capillary electrophoresis and solid phase extraction or filtration, to generate an eluent comprising the enzymatic cleavage product, and wherein step (b) is performed on the eluent.

5. The method of claim 2, wherein the step of partially purifying the enzymatic cleavage product comprises filtration to generate a retained fraction comprising the enzymatic cleavage product, and wherein step (b) is performed on the retained fraction.

6. The method of claim 2, wherein the step of partially purifying the enzymatic cleavage product comprises an affinity enrichment of the enzymatic cleavage product, and wherein step (b) is performed on affinity enriched enzymatic cleavage product.

7. The method of claim 6, wherein the affinity enrichment uses one or more of an immobilized metal affinity resin, an antibody, an antibody fragment, streptavidin, protein-G, protein-A or an aptamer.

8. The method of claim 2, further comprising, between step (a) and (b), and prior to the partial purification step, a step of terminating the enzymatic cleavage in the sample being incubated.

9. The method of claim 8, wherein the terminating step comprises one or more of: adding a precipitating reagent to the sample being incubated; adjusting pH of the sample being incubated below pH 5 or above pH 9; heating the sample being incubated to a temperature above 50 degrees Centigrade; cooling the sample being incubated to a temperature below 15 degrees Centigrade; or adding an inhibitor of ADAMTS13 to the sample being incubated.

10. The method of claim 1, wherein the exogenous peptide substrate has at least 90% sequence identity to SEQ ID NO:3.

11. The method of claim 1, wherein the enzymatic cleavage product comprises SEQ ID NO:4.

12. The method of claim 1, wherein step (b) comprises ionizing the enzymatic cleavage product using an ionization technique comprising at least one of electrospray ionization, atmospheric pressure chemical ionization and atmospheric pressure photoionization.

13. The method of claim 1, wherein step (c) uses ions having a mass/charge ratio (m/z) comprising at least one of 602.8±2, 182.1±2, 281.1±2, 462.7±2, 512.3±2, 600.3±2, 605.3±2, 811.4±2, 924.5±2 and 1023.5±2.

14. The method of claim 1, wherein step (c) includes determining specific activity of ADAMTS13.

15. The method of claim 1, wherein an internal standard is added to the sample at any one of the following time points: (i) prior to step (a); (ii) during step (a); or (iii) after step (a), but prior to step (b), and wherein presence or amount of the internal standard is determined along with the presence or the amount of the enzymatic cleavage product in step (c).

16. The method of claim 1, wherein presence or amount of an internal standard is determined along with the presence or the amount of the enzymatic cleavage product in step (c), and wherein the internal standard is an isotopically labelled equivalent of the enzymatic cleavage product.

17. The method of claim 16, wherein a ratio between the determined amount of the internal standard and the determined amount of the enzymatic cleavage product is indicative of the amount of the enzymatic cleavage product formed in step (a) and/or of the amount of activity of ADAMTS13 in the sample.

18. The method of claim 1, wherein the sample is a sample of a biological fluid obtained from a patient.

19. The method of claim 18, wherein the biological fluid is plasma or serum.

20. The method of claim 8, further comprising, between steps (a) and (b), and either before or after the partial purification step, but after the termination step, a step of modifying molecular structure of the enzymatic cleavage product.

21. The method of claim 20, wherein the modifying step comprises further hydrolysis of the enzymatic cleavage product.

22. The method of claim 21, wherein the hydrolysis is performed using an enzyme or a chemical reagent.

23. The method of claim 21, wherein the hydrolysis is performed using at least one of trypsin, pepsin, LysC, formic acid or cyanogen bromide.

24. The method of claim 20, wherein the enzymatic cleavage product is derivatized during the modifying step.

25. The method of claim 24, wherein the derivatization is an enzymatically catalyzed derivatization or a chemical addition.

26. The method of claim 1, further comprising generating a report reciting the amount of activity of ADAMTS13 in the sample, wherein the sample is obtained from a patient, and wherein the report is useful for diagnosing a disease or condition associated with reduced activity of enzyme disintegrin and metalloproteinase with a thrombospondin type 1 motif, member 13 (ADAMTS13) in the patient.

27. The method of claim 26, wherein the disease or the condition is thrombotic thrombocytopenic purpura.

28. The method of claim 1, wherein the enzymatic cleavage product comprises a sequence with at least 90% sequence identity to SEQ ID NO:4.

29. The method of claim 1, wherein the enzymatic cleavage product consists of a sequence with at least 90% sequence identity to SEQ ID NO:4.

* * * * *

SEQUENCE LISTING

<160> NUMBER OF SEQ ID NOS: 8

<210> SEQ ID NO 1
<211> LENGTH: 2050
<212> TYPE: PRT
<213> ORGANISM: Homo sapiens

<400> SEQUENCE: 1

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365
```

-continued

```
Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
            515                 520                 525

Glu Phe Glu Val Leu Lys Ala Phe Val Val Asp Met Met Glu Arg Leu
            530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Thr Leu Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
            645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
            675                 680                 685

Glu Ile Val Ser Tyr Leu Cys Asp Leu Ala Pro Glu Ala Pro Pro Pro
            690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
            725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
            755                 760                 765

Gln Asp Ser Ile His Val Thr Val Leu Gln Tyr Ser Tyr Met Val Thr
770                 775                 780

Val Glu Tyr Pro Phe Ser Glu Ala Gln Ser Lys Gly Asp Ile Leu Gln
```

```
            785                 790                 795                 800
Arg Val Arg Glu Ile Arg Tyr Gln Gly Gly Asn Arg Thr Asn Thr Gly
                    805                 810                 815
Leu Ala Leu Arg Tyr Leu Ser Asp His Ser Phe Leu Val Ser Gln Gly
                    820                 825                 830
Asp Arg Glu Gln Ala Pro Asn Leu Val Tyr Met Val Thr Gly Asn Pro
                    835                 840                 845
Ala Ser Asp Glu Ile Lys Arg Leu Pro Gly Asp Ile Gln Val Val Pro
        850                 855                 860
Ile Gly Val Gly Pro Asn Ala Asn Val Gln Glu Leu Glu Arg Ile Gly
865                 870                 875                 880
Trp Pro Asn Ala Pro Ile Leu Ile Gln Asp Phe Glu Thr Leu Pro Arg
                    885                 890                 895
Glu Ala Pro Asp Leu Val Leu Gln Arg Cys Cys Ser Gly Glu Gly Leu
                    900                 905                 910
Gln Ile Pro Thr Leu Ser Pro Ala Pro Asp Cys Ser Gln Pro Leu Asp
                    915                 920                 925
Val Ile Leu Leu Leu Asp Gly Ser Ser Ser Phe Pro Ala Ser Tyr Phe
        930                 935                 940
Asp Glu Met Lys Ser Phe Ala Lys Ala Phe Ile Ser Lys Ala Asn Ile
945                 950                 955                 960
Gly Pro Arg Leu Thr Gln Val Ser Val Leu Gln Tyr Gly Ser Ile Thr
                    965                 970                 975
Thr Ile Asp Val Pro Trp Asn Val Val Pro Glu Lys Ala His Leu Leu
                    980                 985                 990
Ser Leu Val Asp Val Met Gln Arg Glu Gly Gly Pro Ser Gln Ile Gly
            995                 1000                1005
Asp Ala Leu Gly Phe Ala Val Arg Tyr Leu Thr Ser Glu Met His
        1010                1015                1020
Gly Ala Arg Pro Gly Ala Ser Lys Ala Val Val Ile Leu Val Thr
        1025                1030                1035
Asp Val Ser Val Asp Ser Val Asp Ala Ala Ala Asp Ala Ala Arg
        1040                1045                1050
Ser Asn Arg Val Thr Val Phe Pro Ile Gly Ile Gly Asp Arg Tyr
        1055                1060                1065
Asp Ala Ala Gln Leu Arg Ile Leu Ala Gly Pro Ala Gly Asp Ser
        1070                1075                1080
Asn Val Val Lys Leu Gln Arg Ile Glu Asp Leu Pro Thr Met Val
        1085                1090                1095
Thr Leu Gly Asn Ser Phe Leu His Lys Leu Cys Ser Gly Phe Val
        1100                1105                1110
Arg Ile Cys Met Asp Glu Asp Gly Asn Glu Lys Arg Pro Gly Asp
        1115                1120                1125
Val Trp Thr Leu Pro Asp Gln Cys His Thr Val Thr Cys Gln Pro
        1130                1135                1140
Asp Gly Gln Thr Leu Leu Lys Ser His Arg Val Asn Cys Asp Arg
        1145                1150                1155
Gly Leu Arg Pro Ser Cys Pro Asn Ser Gln Ser Pro Val Lys Val
        1160                1165                1170
Glu Glu Thr Cys Gly Cys Arg Trp Thr Cys Pro Cys Val Cys Thr
        1175                1180                1185
Gly Ser Ser Thr Arg His Ile Val Thr Phe Asp Gly Gln Asn Phe
        1190                1195                1200
```

-continued

```
Lys Leu Thr Gly Ser Cys Ser Tyr Val Leu Phe Gln Asn Lys Glu
    1205            1210                1215

Gln Asp Leu Glu Val Ile Leu His Asn Gly Ala Cys Ser Pro Gly
    1220            1225                1230

Ala Arg Gln Gly Cys Met Lys Ser Ile Glu Val Lys His Ser Ala
    1235            1240                1245

Leu Ser Val Glu Leu His Ser Asp Met Glu Val Thr Val Asn Gly
    1250            1255                1260

Arg Leu Val Ser Val Pro Tyr Val Gly Gly Asn Met Glu Val Asn
    1265            1270                1275

Val Tyr Gly Ala Ile Met His Glu Val Arg Phe Asn His Leu Gly
    1280            1285                1290

His Ile Phe Thr Phe Thr Pro Gln Asn Asn Glu Phe Gln Leu Gln
    1295            1300                1305

Leu Ser Pro Lys Thr Phe Ala Ser Lys Thr Tyr Gly Leu Cys Gly
    1310            1315                1320

Ile Cys Asp Glu Asn Gly Ala Asn Asp Phe Met Leu Arg Asp Gly
    1325            1330                1335

Thr Val Thr Thr Asp Trp Lys Thr Leu Val Gln Glu Trp Thr Val
    1340            1345                1350

Gln Arg Pro Gly Gln Thr Cys Gln Pro Ile Leu Glu Glu Gln Cys
    1355            1360                1365

Leu Val Pro Asp Ser Ser His Cys Gln Val Leu Leu Leu Pro Leu
    1370            1375                1380

Phe Ala Glu Cys His Lys Val Leu Ala Pro Ala Thr Phe Tyr Ala
    1385            1390                1395

Ile Cys Gln Gln Asp Ser Cys His Gln Glu Gln Val Cys Glu Val
    1400            1405                1410

Ile Ala Ser Tyr Ala His Leu Cys Arg Thr Asn Gly Val Cys Val
    1415            1420                1425

Asp Trp Arg Thr Pro Asp Phe Cys Ala Met Ser Cys Pro Pro Ser
    1430            1435                1440

Leu Val Tyr Asn His Cys Glu His Gly Cys Pro Arg His Cys Asp
    1445            1450                1455

Gly Asn Val Ser Ser Cys Gly Asp His Pro Ser Glu Gly Cys Phe
    1460            1465                1470

Cys Pro Pro Asp Lys Val Met Leu Glu Gly Ser Cys Val Pro Glu
    1475            1480                1485

Glu Ala Cys Thr Gln Cys Ile Gly Glu Asp Gly Val Gln His Gln
    1490            1495                1500

Phe Leu Glu Ala Trp Val Pro Asp His Gln Pro Cys Gln Ile Cys
    1505            1510                1515

Thr Cys Leu Ser Gly Arg Lys Val Asn Cys Thr Thr Gln Pro Cys
    1520            1525                1530

Pro Thr Ala Lys Ala Pro Thr Cys Gly Leu Cys Glu Val Ala Arg
    1535            1540                1545

Leu Arg Gln Asn Ala Asp Gln Cys Cys Pro Glu Tyr Glu Cys Val
    1550            1555                1560

Cys Asp Pro Val Ser Cys Asp Leu Pro Pro Val Pro His Cys Glu
    1565            1570                1575

Arg Gly Leu Gln Pro Thr Leu Thr Asn Pro Gly Glu Cys Arg Pro
    1580            1585                1590
```

```
Asn Phe Thr Cys Ala Cys Arg Lys Glu Glu Cys Lys Arg Val Ser
    1595                1600                1605

Pro Pro Ser Cys Pro Pro His Arg Leu Pro Thr Leu Arg Lys Thr
    1610                1615                1620

Gln Cys Cys Asp Glu Tyr Glu Cys Ala Cys Asn Cys Val Asn Ser
    1625                1630                1635

Thr Val Ser Cys Pro Leu Gly Tyr Leu Ala Ser Thr Ala Thr Asn
    1640                1645                1650

Asp Cys Gly Cys Thr Thr Thr Cys Leu Pro Asp Lys Val Cys
    1655                1660                1665

Val His Arg Ser Thr Ile Tyr Pro Val Gly Gln Phe Trp Glu Glu
    1670                1675                1680

Gly Cys Asp Val Cys Thr Cys Thr Asp Met Glu Asp Ala Val Met
    1685                1690                1695

Gly Leu Arg Val Ala Gln Cys Ser Gln Lys Pro Cys Glu Asp Ser
    1700                1705                1710

Cys Arg Ser Gly Phe Thr Tyr Val Leu His Glu Gly Glu Cys Cys
    1715                1720                1725

Gly Arg Cys Leu Pro Ser Ala Cys Glu Val Val Thr Gly Ser Pro
    1730                1735                1740

Arg Gly Asp Ser Gln Ser Ser Trp Lys Ser Val Gly Ser Gln Trp
    1745                1750                1755

Ala Ser Pro Glu Asn Pro Cys Leu Ile Asn Glu Cys Val Arg Val
    1760                1765                1770

Lys Glu Glu Val Phe Ile Gln Gln Arg Asn Val Ser Cys Pro Gln
    1775                1780                1785

Leu Glu Val Pro Val Cys Pro Ser Gly Phe Gln Leu Ser Cys Lys
    1790                1795                1800

Thr Ser Ala Cys Cys Pro Ser Cys Arg Cys Glu Arg Met Glu Ala
    1805                1810                1815

Cys Met Leu Asn Gly Thr Val Ile Gly Pro Gly Lys Thr Val Met
    1820                1825                1830

Ile Asp Val Cys Thr Thr Cys Arg Cys Met Val Gln Val Gly Val
    1835                1840                1845

Ile Ser Gly Phe Lys Leu Glu Cys Arg Lys Thr Thr Cys Asn Pro
    1850                1855                1860

Cys Pro Leu Gly Tyr Lys Glu Glu Asn Asn Thr Gly Glu Cys Cys
    1865                1870                1875

Gly Arg Cys Leu Pro Thr Ala Cys Thr Ile Gln Leu Arg Gly Gly
    1880                1885                1890

Gln Ile Met Thr Leu Lys Arg Asp Glu Thr Leu Gln Asp Gly Cys
    1895                1900                1905

Asp Thr His Phe Cys Lys Val Asn Glu Arg Gly Glu Tyr Phe Trp
    1910                1915                1920

Glu Lys Arg Val Thr Gly Cys Pro Pro Phe Asp Glu His Lys Cys
    1925                1930                1935

Leu Ala Glu Gly Gly Lys Ile Met Lys Ile Pro Gly Thr Cys Cys
    1940                1945                1950

Asp Thr Cys Glu Glu Pro Glu Cys Asn Asp Ile Thr Ala Arg Leu
    1955                1960                1965

Gln Tyr Val Lys Val Gly Ser Cys Lys Ser Glu Val Glu Val Asp
    1970                1975                1980

Ile His Tyr Cys Gln Gly Lys Cys Ala Ser Lys Ala Met Tyr Ser
```

```
                1985                1990                1995
Ile Asp Ile Asn Asp Val Gln Asp Gln Cys Ser Cys Cys Ser Pro
                2000                2005                2010

Thr Arg Thr Glu Pro Met Gln Val Ala Leu His Cys Thr Asn Gly
                2015                2020                2025

Ser Val Val Tyr His Glu Val Leu Asn Ala Met Glu Cys Lys Cys
                2030                2035                2040

Ser Pro Arg Lys Cys Ser Lys
                2045                2050

<210> SEQ ID NO 2
<211> LENGTH: 210
<212> TYPE: PRT
<213> ORGANISM: Homo sapiens

<400> SEQUENCE: 2

Asp Leu Ala Pro Glu Ala Pro Pro Thr Leu Pro Pro Asp Met Ala
1               5                   10                  15

Gln Val Thr Val Gly Pro Gly Leu Leu Gly Val Ser Thr Leu Pro
                20                  25                  30

Lys Arg Asn Ser Met Val Leu Asp Val Ala Phe Val Leu Glu Gly Ser
            35                  40                  45

Asp Lys Ile Gly Glu Ala Asp Phe Asn Arg Ser Lys Glu Phe Met Glu
    50                  55                  60

Glu Val Ile Gln Arg Met Asp Val Gly Gln Asp Ser Ile His Val Thr
65                  70                  75                  80

Val Leu Gln Tyr Ser Tyr Met Val Thr Val Glu Tyr Pro Phe Ser Glu
                85                  90                  95

Ala Gln Ser Lys Gly Asp Ile Leu Gln Arg Val Arg Glu Ile Arg Tyr
            100                 105                 110

Gln Gly Gly Asn Arg Thr Asn Thr Gly Leu Ala Leu Arg Tyr Leu Ser
        115                 120                 125

Asp His Ser Phe Leu Val Ser Gln Gly Asp Arg Glu Gln Ala Pro Asn
    130                 135                 140

Leu Val Tyr Met Val Thr Gly Asn Pro Ala Ser Asp Glu Ile Lys Arg
145                 150                 155                 160

Leu Pro Gly Asp Ile Gln Val Val Pro Ile Gly Val Gly Pro Asn Ala
                165                 170                 175

Asn Val Gln Glu Leu Glu Arg Ile Gly Trp Pro Asn Ala Pro Ile Leu
            180                 185                 190

Ile Gln Asp Phe Glu Thr Leu Pro Arg Glu Ala Pro Asp Leu Val Leu
        195                 200                 205

Gln Arg
210

<210> SEQ ID NO 3
<211> LENGTH: 73
<212> TYPE: PRT
<213> ORGANISM: Artificial Sequence
<220> FEATURE:
<223> OTHER INFORMATION: Synthetic Construct

<400> SEQUENCE: 3

Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30
```

```
Ile Gly Val Gly Pro Asn Ala Asn Val Gln Glu Leu Glu Arg Ile Gly
            35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Asp Arg Glu Gln Ala Pro Asn Leu Val Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: X = [13C,15N]-Leucine

<400> SEQUENCE: 5

Asp Arg Glu Gln Ala Pro Asn Xaa Val Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Glu Gln Lys Leu Ile Ser Glu Glu Asp Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Asp Tyr Lys Asp Asp Asp Asp Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

His His His His His His
1               5
```